United States Patent
Zanelli et al.

(10) Patent No.: US 8,790,665 B2
(45) Date of Patent: Jul. 29, 2014

(54) SERUM PROTEIN-BASED DETECTION OF RANDOM SEQUENCE POLYMER COMPOSITIONS

(75) Inventors: Eric H. Zanelli, Sudbury, MA (US); Jeff Krieger, Newtonville, MA (US); Joe Connolly, Natick, MA (US); Kathryn H. Collins, Plymouth, MA (US)

(73) Assignee: Ares Trading SA, Vaud (CH)

( * ) Notice: Subject to any disclaimer, the term of this patent is extended or adjusted under 35 U.S.C. 154(b) by 0 days.

(21) Appl. No.: 13/510,021

(22) PCT Filed: Nov. 17, 2010

(86) PCT No.: PCT/US2010/057108
§ 371 (c)(1), (2), (4) Date: Jul. 11, 2012

(87) PCT Pub. No.: WO2011/063045
PCT Pub. Date: May 26, 2011

(65) Prior Publication Data
US 2012/0276135 A1 Nov. 1, 2012

Related U.S. Application Data

(60) Provisional application No. 61/281,470, filed on Nov. 17, 2009, provisional application No. 61/386,909, filed on Sep. 27, 2010.

(51) Int. Cl.
*A61K 39/00* (2006.01)
*C07K 1/22* (2006.01)
*C07K 1/00* (2006.01)
*G01N 33/68* (2006.01)

(52) U.S. Cl.
CPC ... *C07K 1/22* (2013.01); *C07K 1/00* (2013.01); *G01N 33/68* (2013.01)
USPC .................. 424/280.1; 424/185.1; 424/193.1; 435/7.1

(58) Field of Classification Search
CPC ............. A61K 38/00; A61K 2039/555; C07K 2319/00
USPC ................... 424/185.1, 193.1, 280.1; 435/7.1
See application file for complete search history.

(56) References Cited

U.S. PATENT DOCUMENTS

2002/0182210 A1    12/2002 Rodriguez et al.
2003/0157561 A1*   8/2003 Kolkman et al. .............. 435/7.1

(Continued)

FOREIGN PATENT DOCUMENTS

WO    2005/074579    8/2005
WO    2008/157697    12/2008

OTHER PUBLICATIONS

Teitelbaum et al., Cross-reactions and specificities of monoclonal antibodies against myelin basic protein and against the synthetic copolymer 1, PNAS, vol. 88, No. 21, pp. 9528-9532, Nov. 1, 1991.*
Isoda et al., Lack of Interleukin-1 Receptor Antagonist Modulates Plaque Composition in Apolipoprotein E-Deficient Mice, Apr. 1, 2004, Journal of the American Heart Association, pp. 1068-1073.*

(Continued)

*Primary Examiner* — Melanie Y Brown
*Assistant Examiner* — Rebecca Martinez
(74) *Attorney, Agent, or Firm* — Nixon Peabody LLP; Mark J. FitzGerald; Nicole D. Kling

(57) ABSTRACT

There exist in the art methods of detecting simple peptides. However, methods to determine the effective plasma concentration of mixtures of peptides as a group, rather than for individual peptides with a defined amino acid sequence, are complicated by the heterogeneity of the peptides to be detected. This application provides improved methods of detecting and assessing random sequence polymer (RSP) compositions, methods for the detection and quantitation of RSP compositions, means to determine and enrich a subset of peptides in an RSP composition based on the subset's interactions with certain capture polypeptides, and methods for administering RSP compositions to a subject in need thereof, wherein the dosage regimen and quantity may be determined or evaluated based on the above-mentioned methods for detection and quantitation.

11 Claims, 18 Drawing Sheets

(56) References Cited

U.S. PATENT DOCUMENTS

2006/0020109 A1* 1/2006 Strominger et al. .......... 530/300
2009/0275496 A1  11/2009 Baldwin et al.

OTHER PUBLICATIONS

Pignatelli et al., Tumour necrosis factor alpha upregulates platelet CD40L in patients with heart failure, Feb. 15, 2008, Journal of Cardiovascular Research, pp. 515-522.*

* cited by examiner

FIGURE 3

| PI-2301 lot U0517 with normal mouse serum | | |
|---|---|---|
| protein identification | NCBI locus/accession no. | protein score (average of three significant ID) |
| Apolipoprotein A-I | Q9Z2L4 | 118 |
| vitronectin | AAA40558 | 101 |
| lumican | AAB35361 | 75 |

| Copaxone with normal mouse serum | | |
|---|---|---|
| protein identification | NCBI locus/accession no. | protein score (average of three significant ID) |
| Apolipoprotein A-I | Q9Z2L4 | 125 |
| Inter-alpha-trypsin inhibitor heavy chain H1 | Q61702 | 109 |
| complement component 3 | NP_058690 | 97 |
| Inter-alpha-trypsin inhibitor heavy chain H2 | Q61703 | 89 |
| vitronectin | AAA40558 | 87 |

| Copaxone with normal human serum | | |
|---|---|---|
| protein identification | NCBI locus/accession no. | protein score (average of three significant ID) |
| complement component C3 | AAA85332 | 397 |
| apolipoprotein A-1 preproprotein | AAA51747 | 279 |
| apolipoprotein A-II preproprotein (apolipoprotein D) | NP_001634 (AAB32200) | 208 |
| complement component C4A | AAA51855 | 193 |
| trypsin inhibitor | CAA30160 | 183 |
| inter-alpha-trypsin inhibitor family heavy chain-related protein (IHRP) | BAA07602 | 175 |
| alpha-1-B-glycoprotein | OMHU1B | 160 |
| alpha-1-antitrypsin | AAA51546 | 156 |
| apolipoprotein A-IV | AAA51744 | 147 |

FIGURE 3 (continued)

| Copaxone with normal human serum | | |
|---|---|---|
| ceruloplasmin | AAA51975 | 142 |
| unnamed protein product (BLAST search IDs it as a IgM heavy chain) | CAA34971 | 134 |
| apolipoprotein E | AAB59518 | 129 |
| complement factor B | AAA16820 | 127 |
| prealbumin | BAA00059 | 120 |
| Chain C, Immunoglobulin M | 2RCJ_C | 105 |
| immunoglobulin lambda light chain | CAA40939 | 104 |
| Coagulation factor II (thrombin) | 3F68_H | 103 |
| Ig kappa chain V-III (KAU cold agglutinin) | A23746 | 97 |
| apolipoprotein J precursor | AAA51765 | 97 |
| Ig A1 Bur | 763134A | 92 |
| histidine-rich glycoprotein precursor | NP_000403 | 91 |
| Alpha-2-HS-glycoprotein | P02765 | 82 |
| gelsolin isoform a precursor | NP_000168 | 78 |
| inhibitor,Kunitz type proteinase | 0511271A | 74 |
| unnamed protein product (BLAST search IDs it as vitronectin) | CAA28659 | 72 |
| Ig J-chain | AAA58902 | 67 |

| PI-2301 lot U0517 with normal human serum | | |
|---|---|---|
| protein identification | NCBI locus/accession no. | protein score (average of three significant ID) |
| apolipoprotein A-1 preproprotein | AAA51747 | 495 |
| prealbumin | BAA00059 | 179 |
| apolipoprotein A-IV | AAA51744 | 103 |
| alpha-1-antitrypsin | AAA51546 | 102 |
| apolipoprotein A-II preproprotein (apolipoprotein D) | NP_001634 (AAB32200) | 84 |
| apolipoprotein C-III | AAB59372 | 86 |
| alpha-1-B-glycoprotein | OMHU1B | 85 |

FIGURE 3 (continued)

| in-house PI-2301 acetylated with normal human serum | | |
|---|---|---|
| protein identification | NCBI locus/accession no. | protein score (average of three significant ID) |
| apolipoprotein A-1 preproprotein | AAA51747 | 515 |
| preabumin | BAA00059 | 170 |
| apolipoprotein A-II preproprotein (apolipoprotein D) | NP_001634 (AAB32200) | 123 |
| alpha-1-antitrypsin | AAA51546 | 128 |
| apolipoprotein A-IV | AAA51744 | 143 |
| apolipoprotein C-III | AAB59372 | 100 |
| alpha2-HS glycoprotein | BAA22651 | 88 |
| alpha-1-B-glycoprotein | OMHU1B | 79 |
| apolipoprotein J precursor | AAA51765 | 72 |

| in-house PI-2301 not acetylated with normal human serum | | |
|---|---|---|
| protein identification | NCBI locus/accession no. | protein score (average of three significant ID) |
| apolipoprotein A-1 preproprotein | AAA51747 | 471 |
| alpha-1-antitrypsin | AAA51546 | 209 |
| apolipoprotein A-IV | AAA51744 | 150 |
| preabumin | BAA00059 | 177 |
| apolipoprotein C-III | AAB59372 | 116 |
| apolipoprotein A-II preproprotein (apolipoprotein D) | NP_001634 (AAB32200) | 122 |
| alpha-1-B-glycoprotein | OMHU1B | 84 |
| alpha2-HS glycoprotein | BAA22651 | 86 |

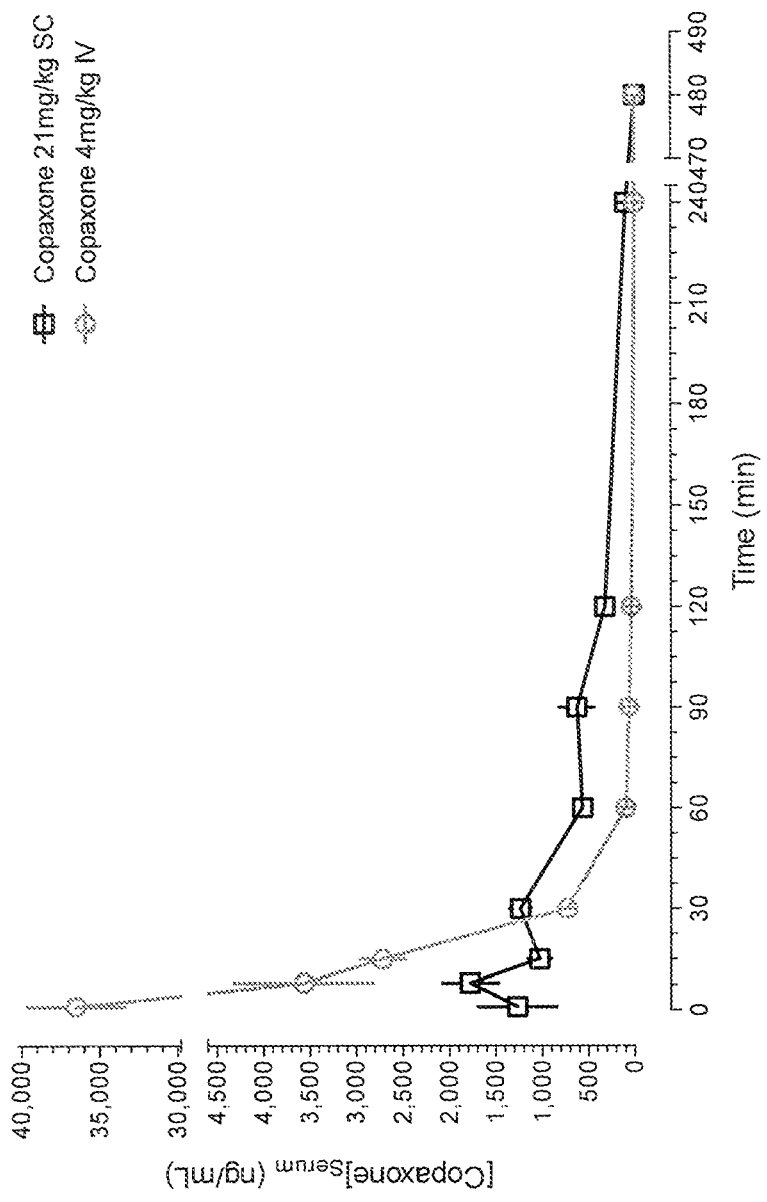

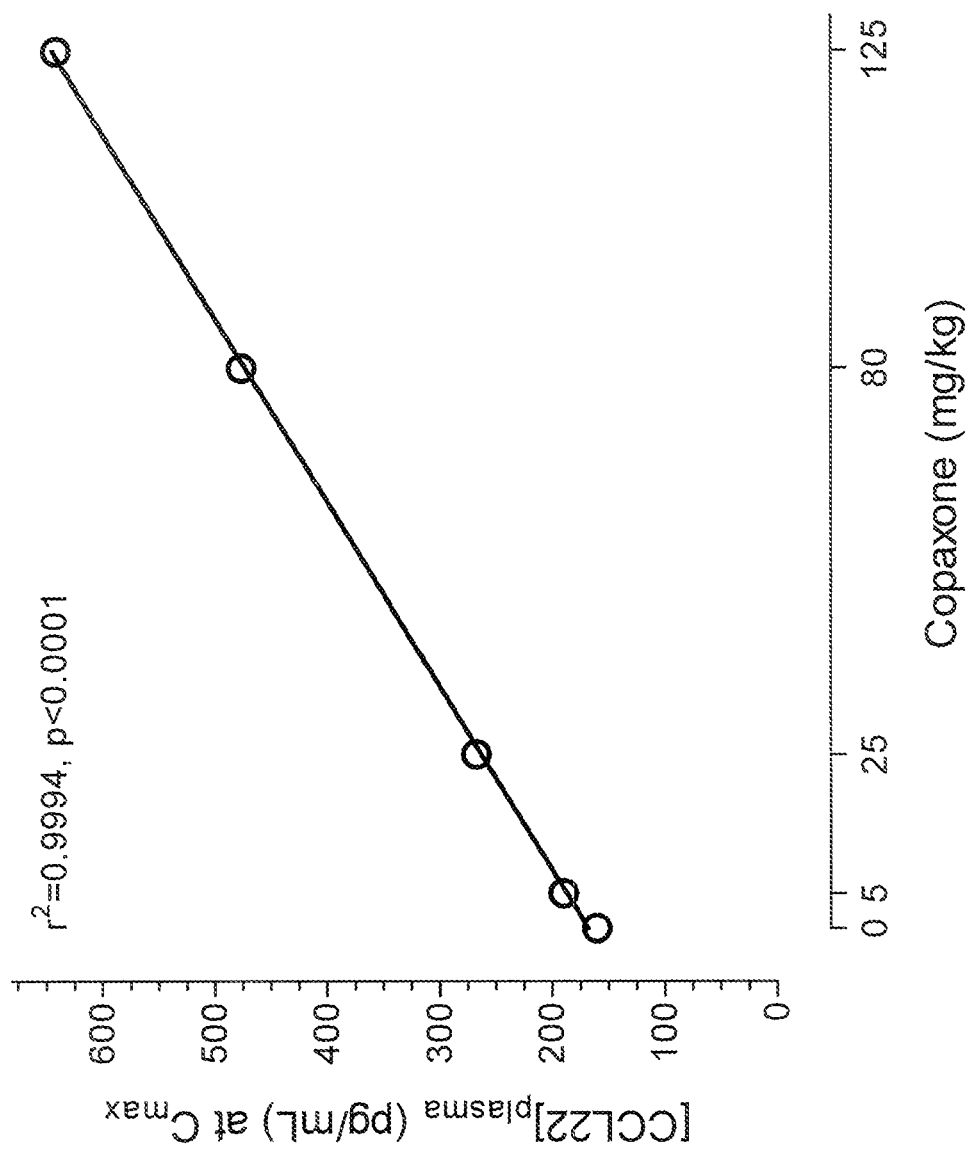
FIGURE 5. Linear correlation between maximum CCL22 plasma concentration and dose of Copaxone® administered SC to mice

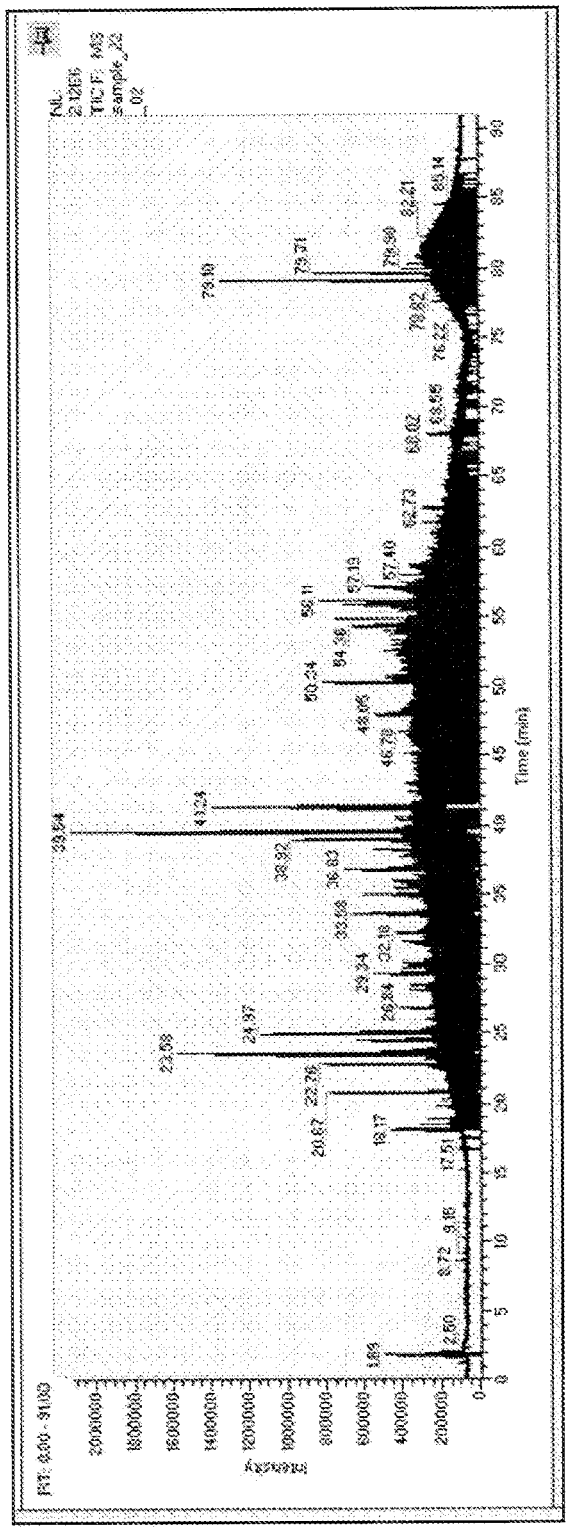
FIGURE 6. Representative peptide patterns observed by LC-MS from serum proteins eluted from YEAK fragments immobilized on a CNBr-Seph column

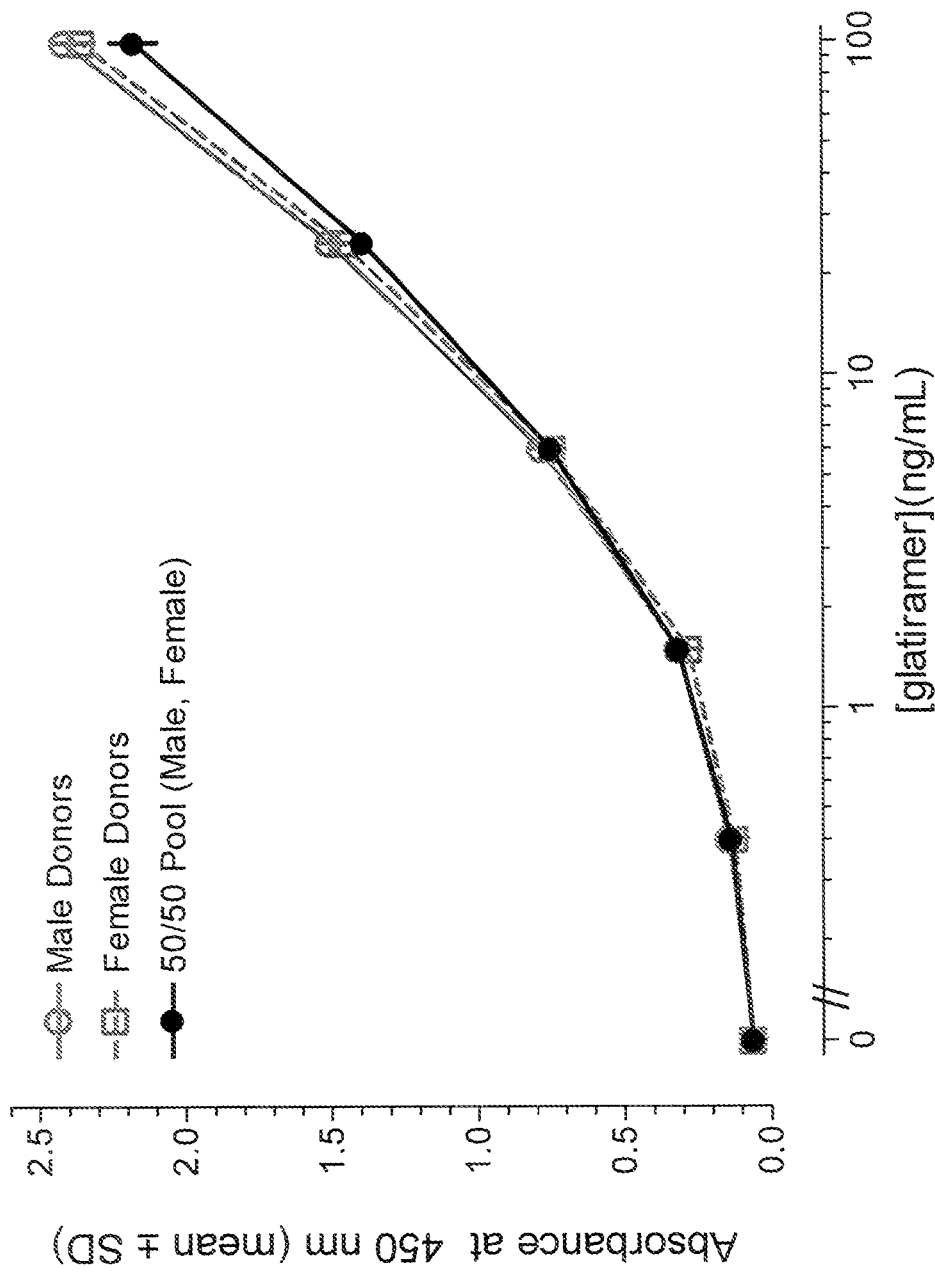
FIGURE 7. Standard curve using the new ELISA assay and spiking of glatiramer acetate into male, female or male/female pooled normal human sera

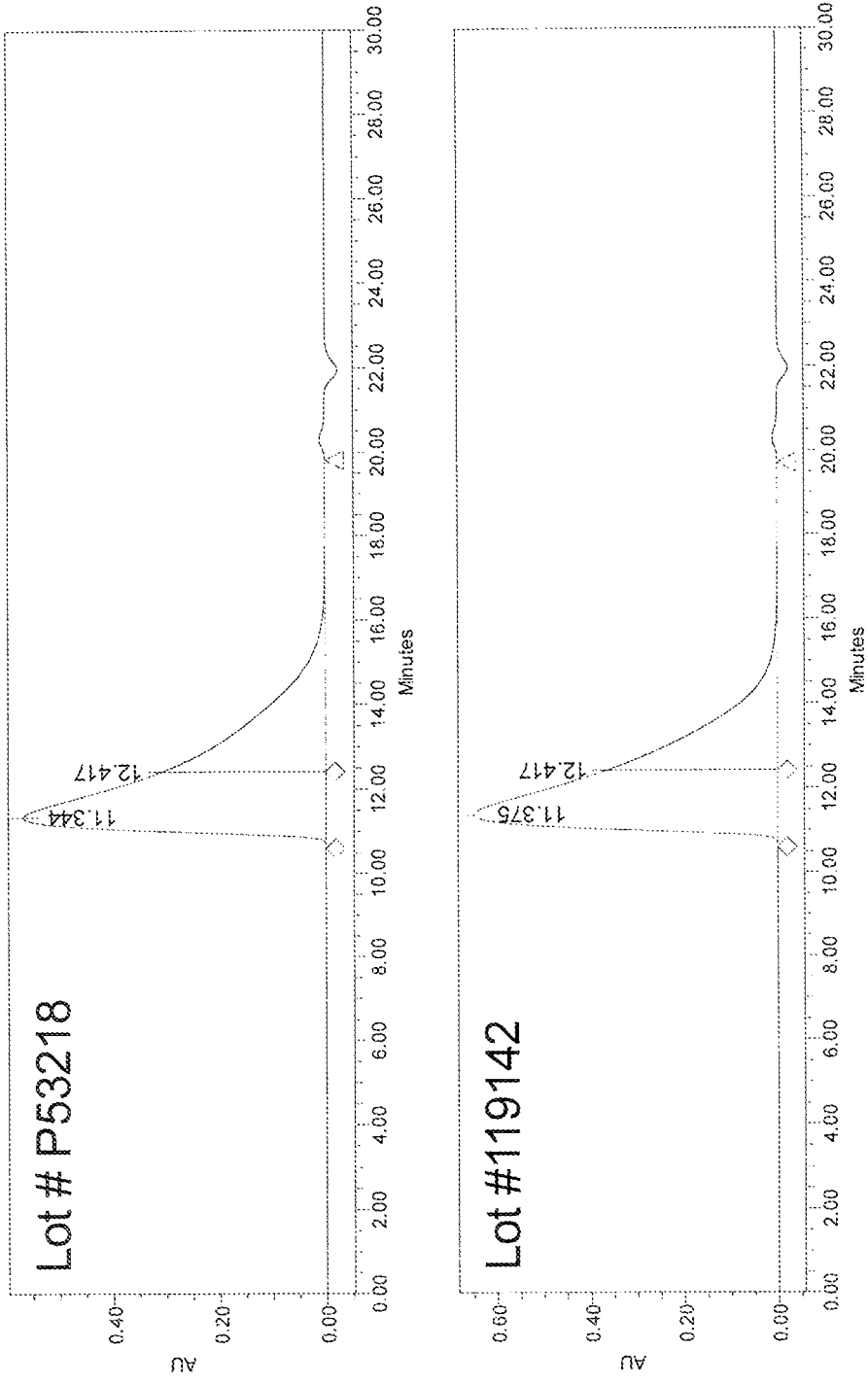

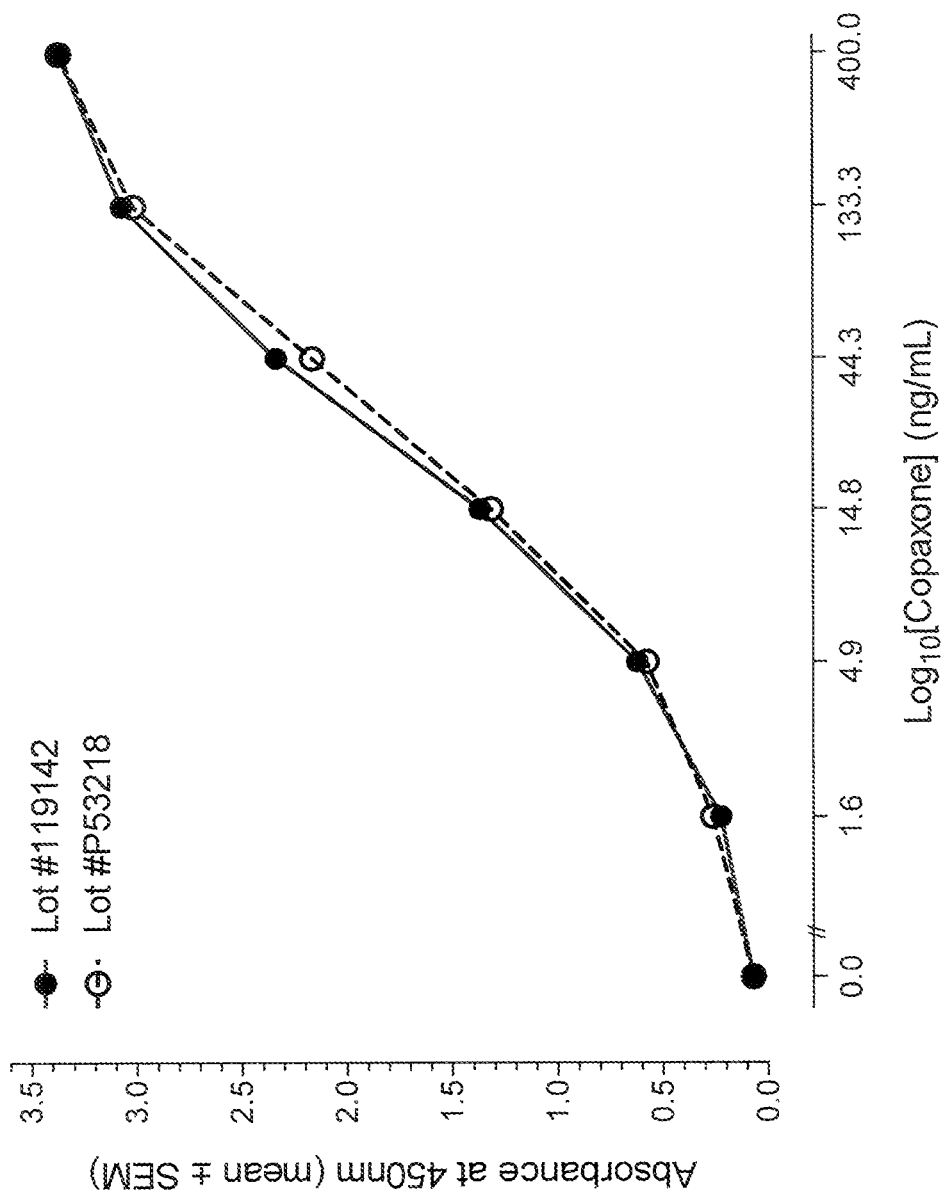
FIGURE 9. Standard curves using the new ELISA assay and comparing Copaxone® lots #P53218 and #119142

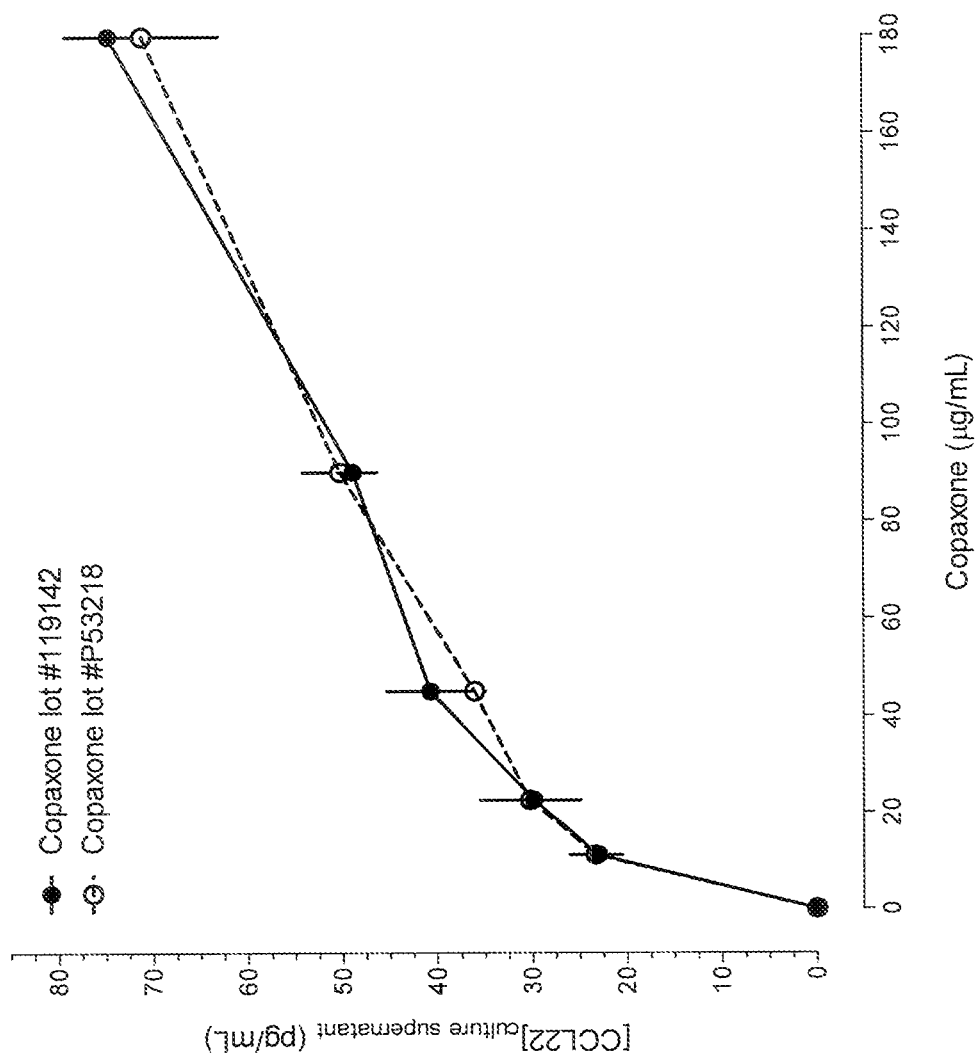
FIGURE 10. CCL22 release in culture medium of monocytes cultured with Copaxone® lots #P53218 and #119142

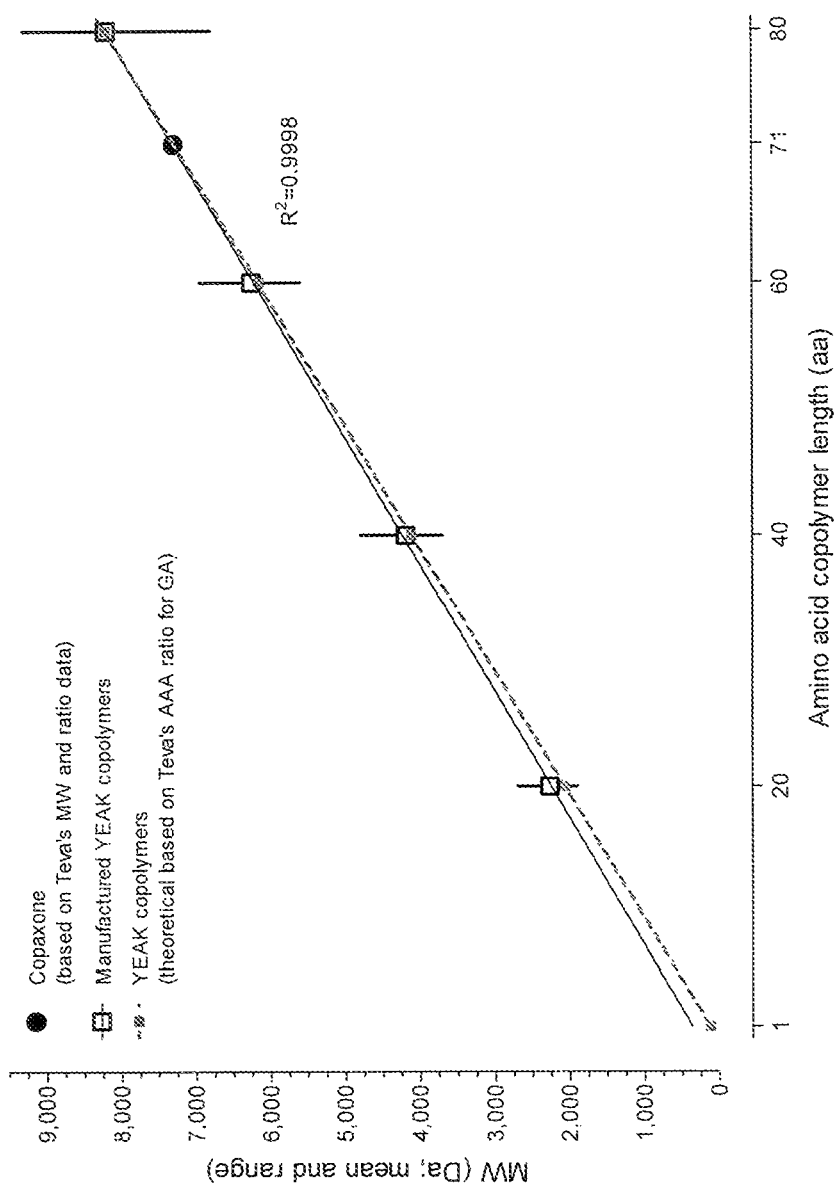
FIGURE 11. Linearity between amino acid length and average molecular weights of YEAK copolymers manufactured by solid phase peptide synthesis

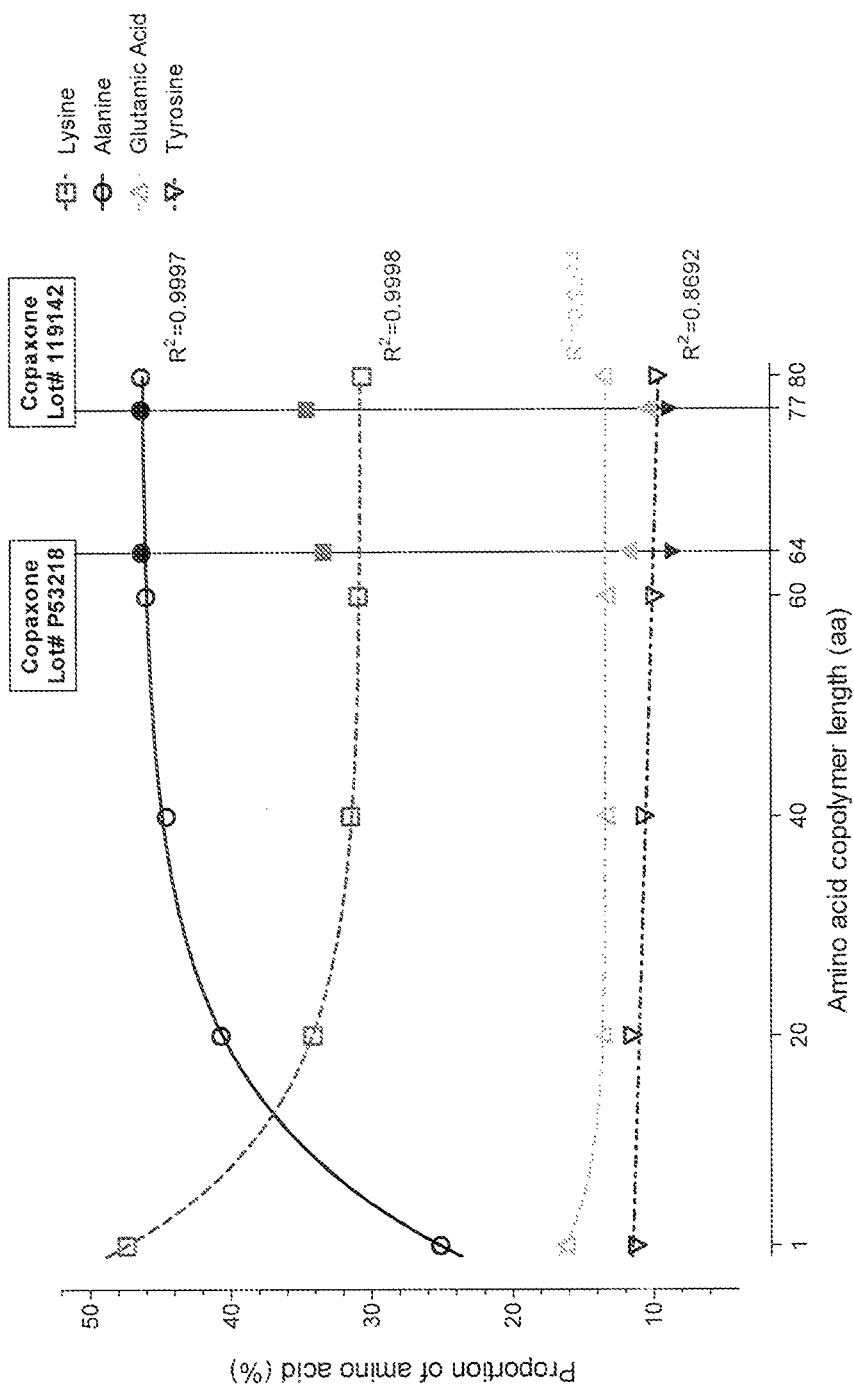
FIGURE 12. Proportion of Y, E, A and K amino acids normalized to 100 amino acids in YEAK copolymers manufactured by solid phase peptide synthesis
Based on amino acid and MALDI-TOF analyses.

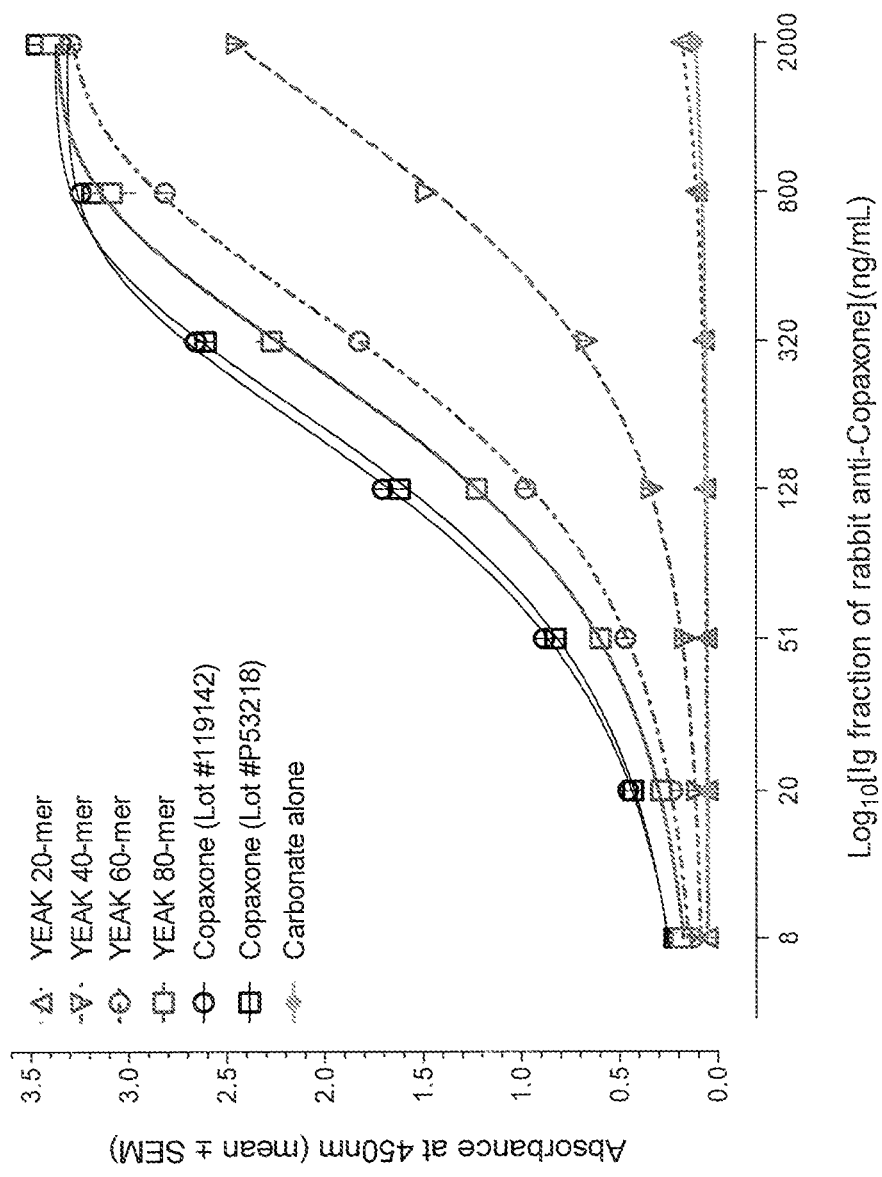
FIGURE 13. Reactivity of the Immunoglobulin fraction of an anti-GA rabbit polyserum against YEAK amino acid cop

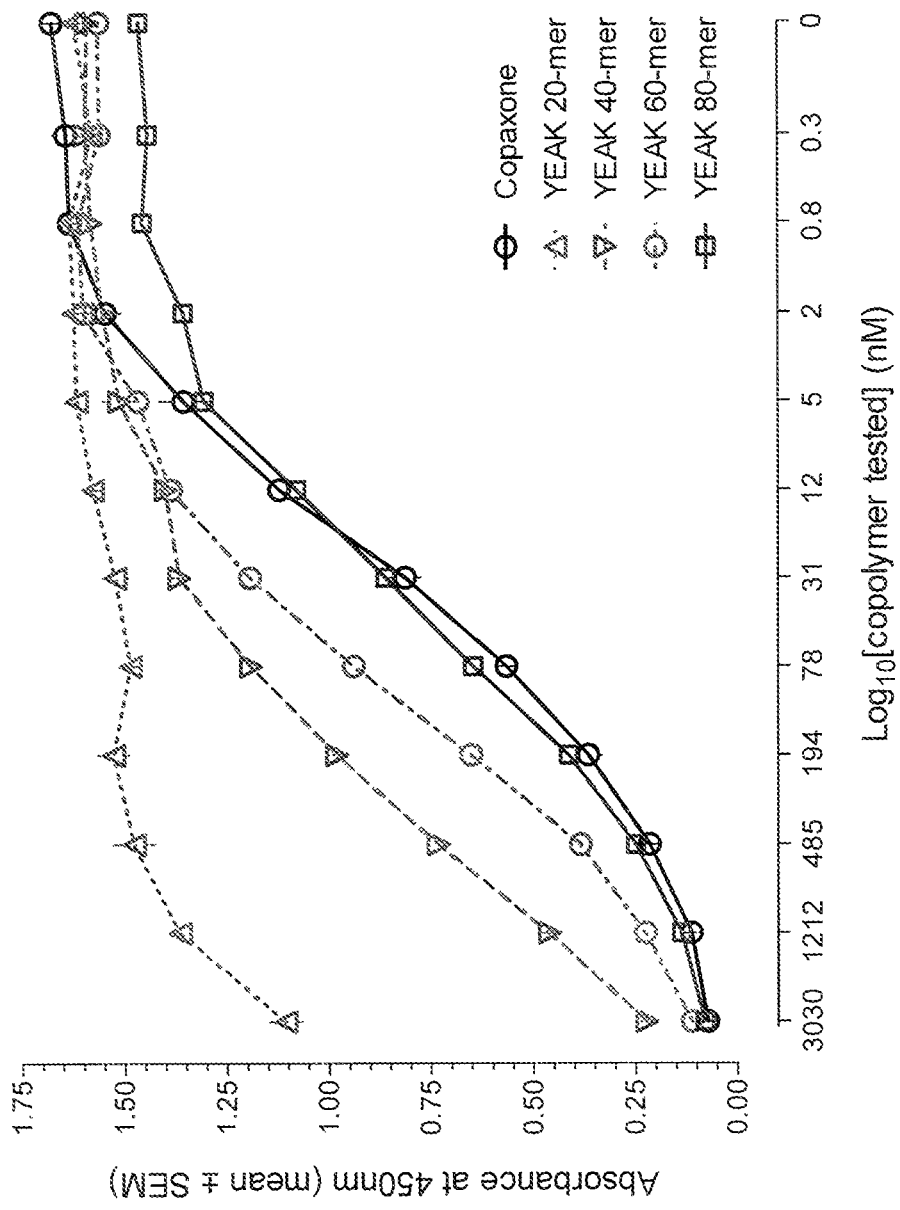
FIGURE 14. Standard curve using a previous PK method and YEAK copolymers compared to Copaxone®

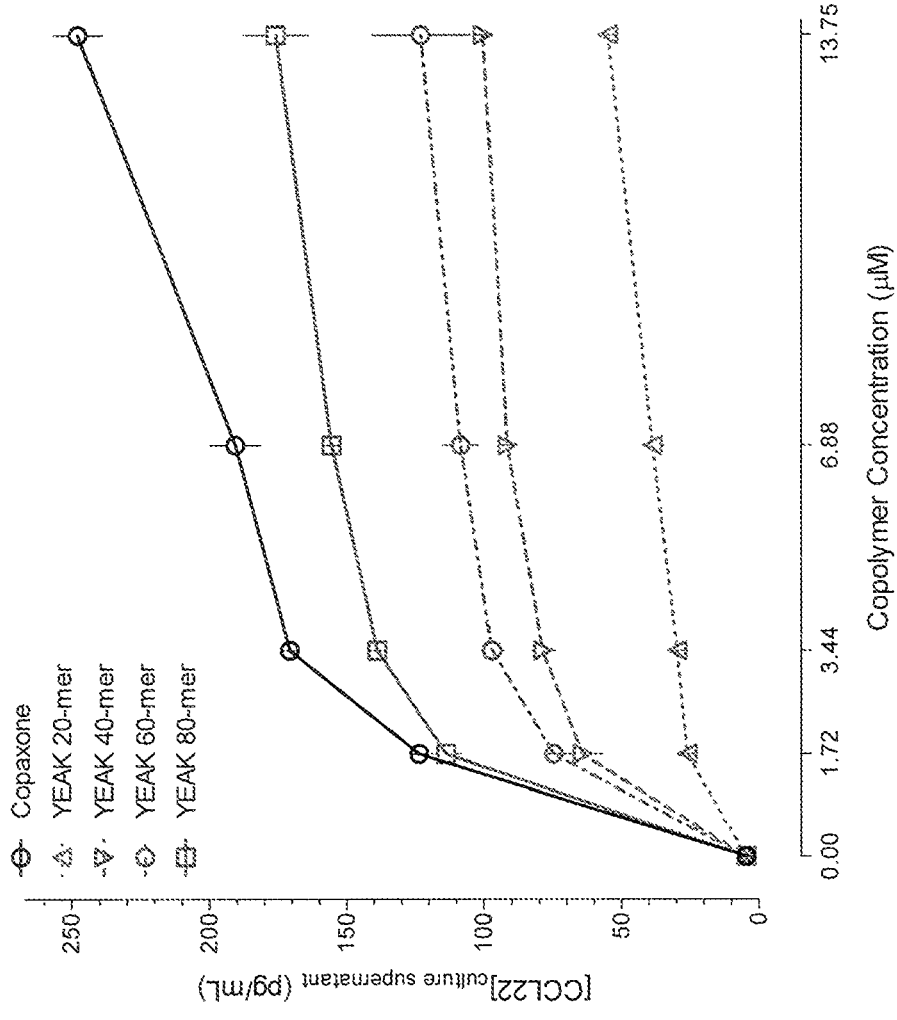

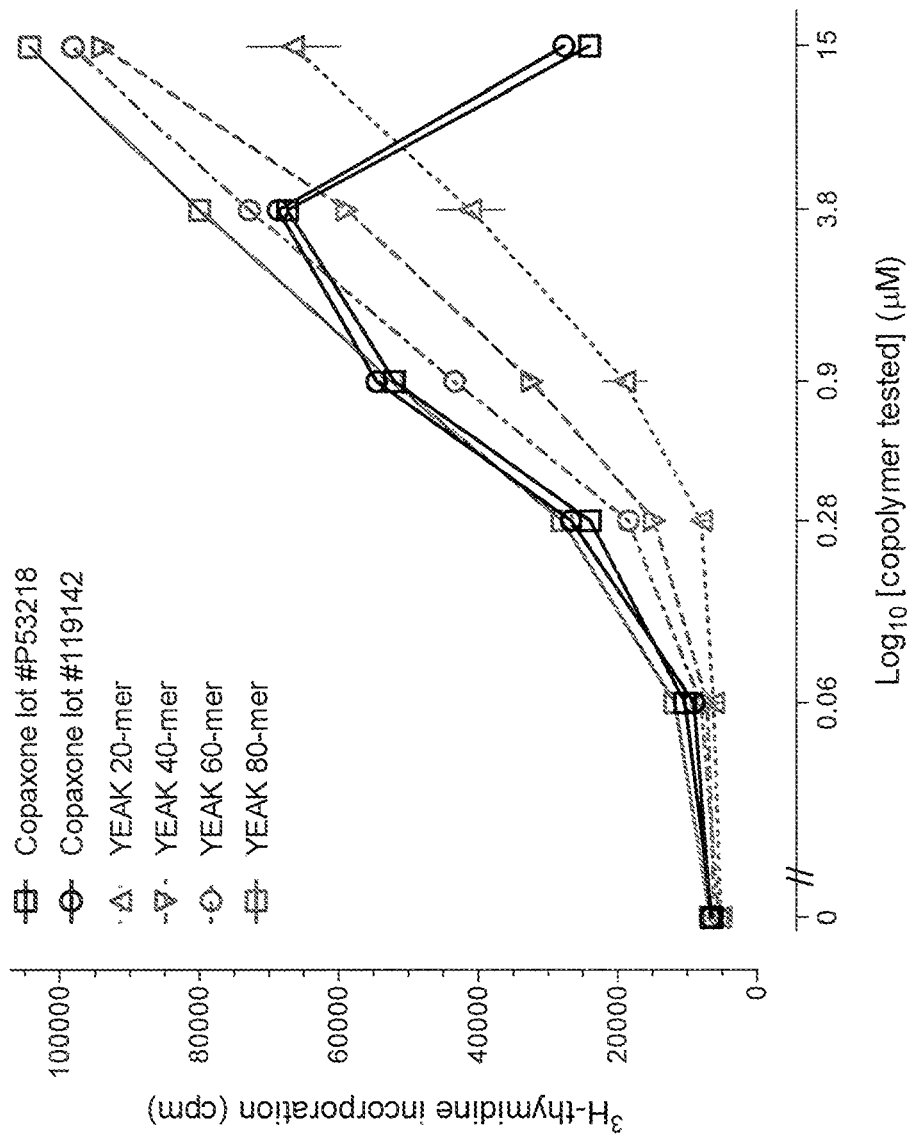
FIGURE 16. Effect of YEAK copolymers on mouse splenocyte recall response

SERUM PROTEIN-BASED DETECTION OF RANDOM SEQUENCE POLYMER COMPOSITIONS

CROSS REFERENCE TO RELATED APPLICATIONS

This application is a 35 U.S.C. §371 National Phase Entry Application of International Application No. PCT/US2010/057108 filed Nov. 17, 2010, which designates the U.S., and which claims benefit under 35 U.S.C. §119(e) of U.S. Provisional Application No. 61/281,470, filed Nov. 17, 2009, and U.S. Provisional Application No. 61/386,909, filed Sep. 27, 2010, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 9, 2012, is named 20120710_SequenceListing-TextFile_033705_072062_US.txt and is 16,277 bytes in size.

BACKGROUND

There exist in the art methods of detecting simple peptides. However, methods to determine the effective plasma concentration of mixtures of peptides as a group, rather than for individual peptides with a defined amino acid sequence, are complicated by the heterogeneity of the peptides to be detected. For example, random sequence polymer (RSP) compositions comprise a complex mixture of amino acids that have been randomly incorporated into peptide chains. RSP compositions are defined according to the identity and ratio of amino acids, not according to a defined sequence. Given this diversity, improved methods for evaluating the consistency and composition of these RSP compositions through multiple manufacturing preparations are needed. Determining the in vivo status of an RSP composition has immunologic significance because, depending on the route and/or frequency of administration and the serum proteins that bind the RSP composition, a mixture can invoke primarily inflammatory ($T_H1$ type) or primarily regulatory ($T_H2$ type) responses, leading to variations in pharmacokinetic and pharmacodynamic effects in the subject. More rigorous design and consistent administration of an RSP composition may increase the therapeutic efficacy, or reduce the potential for adverse inflammatory responses.

Thus, there is a need for methods of quantitative analysis of RSP compositions, e.g., to assist the in vivo evaluation of such mixtures and to determine the suitable amount and means of administration for therapeutic purposes.

SUMMARY OF THE INVENTION

This application provides improved methods of detecting and assessing RSP compositions. The instant invention provides methods for the detection and quantitation of RSP compositions. The instant invention provides a means to determine and enrich a subset of peptides in an RSP composition based on the subset's interactions with certain capture polypeptides. The instant invention further provides methods for administering RSP compositions to a subject in need thereof, wherein the dosage regimen and quantity may be determined or evaluated based on the above-mentioned methods for detection and quantitation.

The present disclosure also provides a method for detecting an RSP composition comprising the steps: (a) affixing said RSP composition to a solid support; (b) contacting said solid support in (a) with a protein-containing biological fluid; (c) identifying the proteins from (b) specifically bound to the solid support in (a); (d) obtaining substantially pure preparations of bound proteins in (c); (e) affixing said proteins in (c) to a means for quantitatively detecting said RSP composition; and (f) determining binding of said RSP composition to each individual said protein in (e).

This disclosure also provides a method for improving the design of an RSP composition comprising the steps: (a) affixing said RSP composition to a solid support; (b) contacting said solid support in (a) with a protein-containing biological fluid; (c) identifying the proteins from (b) specifically bound to the solid support in (a); (d) obtaining substantially pure preparations of bound proteins in (c); (e) affixing said proteins in (c) to a means for quantitatively detecting said RSP composition; (f) determining binding of said RSP composition to each individual said protein in (e); (g) adjusting the design of said RSP composition to either enhance or reduce binding to one or more proteins in (e); (h) repeating step (f); (i) optionally repeating steps (f-h), wherein the adjustments to design of said RSP composition results in any one or more of the group comprising: increased bioavailability, reduction in toxicity, and increase in efficacy.

Furthermore, this application provides a method for detecting species within an RSP composition comprising the steps: (a) affixing said RSP composition to a solid support; (b) contacting said solid support in (a) with a protein-containing biological fluid; (c) identifying the proteins from (b) specifically bound to the solid support in (a); (d) obtaining substantially pure preparations of bound proteins in (c); (e) affixing said proteins in (c) to a solid support; (f) contacting said solid support in (e) with said RSP composition; and (g) determining binding of individual species of said RSP composition to said solid support in (f).

In addition, this application provides a method for improving the design of species within an RSP composition comprising the steps: (a) affixing said RSP composition to a solid support; (b) contacting said solid support in (a) with a protein-containing biological fluid; (c) identifying the proteins from (b) specifically bound to the solid support in (a); (d) obtaining substantially pure preparations of bound proteins in (c); (e) affixing said proteins in (c) to a solid support; (f) contacting said solid support in (e) with said RSP composition; (g) determining binding of individual species of said RSP composition to said solid support in (f); (h) adjusting the design of said RSP composition to either enhance or reduce binding to one or more proteins in (f); (i) repeating step (g); and (j) optionally repeating steps (g-i), wherein the adjustments to design of a species of said RSP composition result in any one or more of the group comprising: increased bioavailability, reduction in toxicity, and increase in efficacy.

Using the methods of the instant application, investigators can not only more reliably detect lower amounts of components of the RSP composition, but also specifically detect species within RSP compositions that are responsible for or contribute towards a biological activity of interest, for example toxicity or efficacy.

A finding that underlies the instant invention is the specific binding of a single peptide or a multiplicity of peptides within an RSP composition by certain proteinaceous materials. Conversely, once such proteinaceous materials, herein termed "capture polypeptides", are identified, one or more of the capture polypeptides can be used to quantitatively analyze peptides of the RSP composition, isolate functionally superior subsets of the peptides within the RSP composition, or classify components of the RSP composition based on the binding specificity. To practice the instant invention, a capture polypeptide that binds to the peptides is identified and prepared in a form useful to practice the instant invention, i.e., isolated and purified to a sufficient degree that its binding to the peptides is not compromised by the presence of other components.

An aspect of the instant invention provides a method to assess or determine variations in the products of distinct manufacturing preparations, different methods of manufacture, or different post-manufacturing processing methods of an RSP composition. A particular method of the invention is to compare the binding of different preparations of an RSP composition to a capture polypeptide to determine the similarities and/or differences between preparations.

A further aspect of the invention provides a method to quantitatively analyze peptides that are found in an RSP composition or a sample comprising an RSP composition. Some embodiments of the invention are methods to determine a biologically available quantity or concentration in vivo (e.g., a plasma concentration) of an administered RSP composition.

A method of the instant invention is to detect the presence of RSP compositions in a subject's tissue, said subject having previously been in contact with or treated with the RSP composition, wherein the method is carried out one or more times immediately after such contact, or after at least about 10, 20, 30, or 45 minutes, or 1, 2, 4, 6, 12, 24, 36, or 48 hours, or 3, 4, 5, 6, 7, or 10 days, or 2, 3, 4, 6, 8, or 12 weeks after such contact. A particular method of the instant invention is to detect the presence of constituents of an RSP composition in the serum or plasma of a mammal, said mammal having been previously treated with said RSP composition prior to carrying out said method within a time period described above. In certain embodiments, said mammal is a human.

In certain embodiments, the method comprises determining the presence of, and optionally the quantity of, RSP compositions by binding the peptides to one or more predetermined capture polypeptides followed by a detection method, such as an immunologic detection method. Thus, one aspect of the invention comprises selecting or identifying a serum protein that preferentially binds an RSP composition. In certain embodiments, a method of identifying one or more serum protein comprises contacting an RSP composition with a biological sample comprising serum, detecting the binding, if any, of peptides in the RSP composition to one or more components of the serum, isolating the bound components, and identifying one or more of the bound components. In some embodiments, the bound components can be isolated by contacting the sample with an affinity column designed to bind the peptides of the RSP composition and subsequently eluting the bound fraction, followed by identifying the bound component(s).

Any serum binding proteins that bind peptides of RSP compositions can be used in the above methods. Suitable detection methods include Direct Competitive Enzyme-Linked Immunosorbent Assay (ELISA), Western blot, immunoflow cytometric detection, radioimmunoassay (RIA), or any other immunologic detection method that allows quantitative detection of specific antigens.

One aspect of the instant invention is a method for detecting the presence of an RSP composition in a biological sample, comprising: contacting the biological sample with at least one capture polypeptide; and detecting the presence or absence of binding of the capture polypeptide to the RSP composition, wherein the presence of binding indicates the presence of peptide components of the RSP composition in the biological sample. Further, such method can be extended to measure the amount or concentration of an RSP composition in a sample.

Another aspect of the instant invention is a method for measuring bioavailability of an RSP composition in a mammal, comprising: administering to a mammal a dose of the RSP composition; removing a biological sample from the subject; and contacting the biological sample with at least one capture polypeptide; thereby determining the bioavailability, or the degree of bioavailability, of the RSP composition in the biological sample.

Another aspect of the instant invention provides methods of administering RSP compositions to a mammalian subject, such amount determined based on the bioavailable portion of the dosed amount as determined by the method described above or other methods described herein. In certain embodiments, the method further comprises including a control sample, performing a pharmacodynamic test to determine changes of physiological markers, such as hormones, enzymes, serum proteins, cytokines, immunomodulators, or an effector or regulator of any of these functional proteins, between the control sample and test samples by comparing the two results, and determining the dosage effective to induce the desired changes in a pharmacodynamic parameter. In certain embodiments, behavioral changes, subjective changes as reported by a subject such as amelioration of pain or a symptom of a disease, or other evidence of indirect effects are observed. In certain embodiments, said mammalian subject is a rodent, such as a mouse or rat. In other embodiments, said subject is human.

Certain embodiments of this aspect of the invention provide a method for determining a suitable dose of an RSP composition to administer to a subject in need thereof, comprising: (a) administering to the subject a dose of the RSP composition; (b) removing a biological sample from the subject; (c) contacting the biological sample with at least one capture polypeptide; (d) determining a level of components of the RSP composition in the biological sample; (e) optionally repeating steps (a) through (d) using a different dose; and (g) comparing the levels to a predetermined suitable level of the RSP composition in the biological sample; wherein the suitable dose is a dose that results in the predetermined suitable level of the RSP composition in the biological sample.

Some embodiments of the invention provide methods to predict a portion of bioavailable fraction of an RSP composition. Such methods comprise contacting a sample comprising an RSP composition with a predetermined capture polypeptide that is found in situ at a site where administration and delivery of such RSP composition is contemplated, and determining binding of the RSP composition to the capture polypeptide. Binding by a large fraction of the RSP composition may be indicative of a larger proportion of peptides that are therapeutically and/or physiologically relevant, and tighter binding (per dissociation constant determination) may be indicative of a protective effect that extends the half-life of those peptides in vivo.

A further aspect of the instant invention provides methods to predict a therapeutically effective amount of an RSP composition to be administered to a subject (e.g., a human subject) based on data obtained from experimental subjects. In certain embodiments, the method comprises administering an RSP composition to a non-human experimental mammalian subject, determining the bioavailable portion of the dosed amount (e.g., using a method of quantitative detection described herein), determining functional read-outs, and predicting a therapeutically effective amount of the RSP composition to be delivered to the therapeutic subject based on the data obtained for the experimental mammalian subject and a correlation ratio between the therapeutic and experimental subjects. For the purposes of the instant invention, a "functional read-out" may be a phenotype or function of the subject, a phenotype or function of cellular material derived from the subject, or the composition of one or more fluids derived from the subject. A functional read-out may additionally or alternatively include a measurement of one or more biosynthetic or metabolic components such as hormones, enzymes, serum proteins, cytokines, chemokines, growth factors, immunomodulators, and an effector or regulator of said functional read-outs. In certain embodiments, the detection step may be repeated at various regular or irregular time intervals to determine the time-course of bioavailability, metabolism, and/or clearance after administration. In certain embodiments, a plasma half-life of the RSP composition as a group may be determined in this manner. In a further embodiment, a half-life of a species within the RSP composition may be determined in this manner. In particular embodiments, the experimental subject is a rodent, such as a mouse or rat.

Yet another aspect of the instant invention provides an efficient and effective method of treating a patient by administering an RSP composition, comprising: preparing an RSP composition by synthesizing peptides (e.g., singly followed by pooling multiple peptides, or simultaneously by using pools of amino acid monomers at each cycle of elongation), preparing a pharmaceutically acceptable formulation of said RSP composition, administering said RSP composition to a subject, obtaining a tissue sample from said subject, determining the amounts and/or concentrations of the RSP composition in said tissue sample, determining a functional read-out, correlating the amounts of the RSP composition to the functional read-out, and adjusting the dosage of the RSP composition to the subject to improve the functional readout.

Another aspect of the invention is a method for treating or preventing an unwanted immune response in a subject, comprising administering to the subject a suitable dose of an RSP composition, wherein such suitable dose is determined by: (i) administering to the subject a dose of the RSP composition; (ii) removing a biological sample from the experimental subject; (iii) contacting the biological sample with at least one capture polypeptide; (iv) determining a level of the capture polypeptide in the biological sample; (v) optionally repeating steps (i) through (iv) using a different dose; and (vi) comparing the level(s) against a predetermined suitable level of the RSP composition in the biological sample; wherein a suitable dose is the dose that results in the predetermined suitable level of the RSP composition in said biological sample.

In some the foregoing aspects and embodiments, the capture polypeptide is labeled. In some embodiments, the capture polypeptides are affixed to solid support. In some embodiments, the complex comprising a capture polypeptide and one or more peptide components of an RSP composition is detected and/or isolated. In particular embodiments, the complex is detected and/or isolated by antibodies specific to the complex but not to the capture polypeptide or to the peptide component of the RSP composition.

Yet another aspect of the instant invention provides a method to isolate a selected subset of the peptides that make up the RSP composition. In particular instances, the subset may consist of peptides having one or more different amino acid sequences. In other instances, capture polypeptides may be used to classify the components of the RSP composition based on the binding specificity.

In certain embodiments, a method for isolating peptides from a sample comprising an RSP composition comprises: (a) contacting the sample with at least one capture polypeptide; and (b) separating peptides that bind to the capture polypeptide from the mixture. In certain such embodiments, the capture polypeptides are affixed to a solid support. In some embodiments, the capture polypeptides are epitope-tagged or labeled. In some embodiments, the method further comprises separating bound peptides from the capture polypeptides in order to isolate the peptides. In particular embodiments, the method further comprises determining the characteristics of the isolated peptides, such as amino acid compositions of the pool of isolated peptides and/or amino acid sequences of the isolated peptides.

In certain embodiments, a method of identifying bioavailable peptides in an RSP composition in a subject comprises: (a) administering the RSP composition to the subject; (b) removing a tissue sample from the subject after conducting step (a); and (c) identifying peptides in the sample that bind to at least one capture peptide.

In certain embodiments, a method of identifying a subset of peptides that bind to a capture polypeptide comprises preparing an RSP composition according to a protocol, contacting said RSP composition with a predetermined capture polypeptide (e.g., that is desirable as in vivo target or carrier), determining the binding of peptides within the RSP composition, identifying characteristics that differentiate the peptides that bind from peptides that do not, and preparing an improved RSP composition reflecting one or more of the differentiating characteristics.

Another aspect of the invention is a method of improving the manufacturing process of a composition comprising an RSP composition. In some embodiments, an RSP composition is designed based on the foregoing method of identifying a subset of peptides that bind to a capture polypeptide. In some embodiments, the RSP composition is designed so that the amino acid composition and/or the amino acid sequence approximates that of the subset of peptides that bound to the capture polypeptide. In some embodiments, the RSP composition has enhanced potency compared to a reference RSP composition, wherein the reference RSP composition is or is substantially the same as the original RSP composition that was contacted with the capture polypeptide. In other embodiments, the RSP composition has lower toxicity compared to the reference RSP composition.

In alternative embodiments, a method comprises preparing an RSP composition according to a protocol, formulating a composition comprising the RSPs, determining the bioavailable amount of the RSPs in said composition by detecting the level or degree of functional read-out, comparing such readout against a standard, and adjusting the protocol or formulation of the composition to obtain a desired bioavailability.

Yet another aspect of the invention is targeting of therapeutic agents to specific tissues by associating an RSP composition (e.g., a reference RSP composition or an improved RSP composition generated by the methods disclosed herein) or a component of an RSP composition with a therapeutic agent of interest, where said RSP composition or component thereof binds to a capture polypeptide that has tissue-specific targeting properties. Such associated agents can be administered to a patient to target the agent to a tissue associated with the corresponding capture polypeptide.

Some embodiments of this aspect of the invention provide a method for delivering a therapeutic agent to a specific tissue in a subject, such method comprising: (a) isolating a peptide tag by contacting an RSP composition with a tissue specific peptide and separating peptides that bind to the tissue specific peptide from the mixture; (b) coupling the peptide tag to a therapeutic agent; and (c) administering the conjugate to a subject. Other embodiments of the invention include a method of preparing such targeted therapeutic agent by step (a) and (b) of the above described method, and a targeted therapeutic prepared thereby.

A further aspect of the instant invention is a composition useful and used in any of the methods described above. An embodiment of this aspect of the invention is a composition for detecting an RSP composition comprising YEAK or YFAK peptides in a biological sample, comprising at least one capture polypeptide. In certain embodiments, the capture polypeptide is selected from a component of normal human sera, normal non-human primate sera, normal rabbit sera, normal mouse sera, normal rat sera, normal ferret sera, normal pig sera, normal dog sera, normal horse sera, normal sheep sera, normal cow sera, a component of mammalian-derived HDL proteome, a component of mammalian-derived LDL proteome, complement component C3, apolipoprotein A-1 preproprotein, apolipoprotein A-II preproprotein (apolipoprotein D), complement component C4A, trypsin inhibitor, inter-alpha-trypsin inhibitor family heavy chain-related protein (IHRP), alpha-1-B-glycoprotein, alpha-1-antitrypsin, apolipoprotein A-IV, ceruloplasmin, unnamed protein product (BLAST search IDs it as a IgM heavy chain), apolipoprotein E, complement factor B, prealbumin, apolipoprotein C-III, alpha2-HS glycoprotein, apolipoprotein J precursor, Chain C, Immunoglobulin M, immunoglobulin lambda light chain, Coagulation factor II (thrombin), Ig kappa chain V-III (KAU cold agglutinin), apolipoprotein J precursor, Ig A1 Bur, histidine-rich glycoprotein precursor, Alpha-2-HS-glycoprotein, gelsolin isoform a precursor, inhibitor Kunitz type proteinase, unnamed protein product (NCBI Locus/Accession No. CAA28659), and Ig J-chain.

In any of the foregoing embodiments and aspects, the RSP composition may comprise either YEAK peptides or YFAK peptides. YFAK or YEAK peptides are known in the art and described below, and are peptides that compose an RSP composition, namely a YFAK RSP composition or a YEAK RSP composition. Further, independent of selecting YFAK or YEAK peptides, in particular embodiments the capture polypeptide may be a serum binding protein. In more particular embodiments, the capture polypeptide is selected from alpha-1-antitrypsin, apolipoprotein A-I, alpha-1-B-glycoprotein, apolipoprotein A-IV, apolipoprotein D, and prealbumin, or from the capture polypeptides enumerated in the paragraph immediately preceding this paragraph, or from serum polypeptides disclosed herein.

Further, in any of the foregoing embodiments, the binding of peptides in an RSP composition to a capture polypeptide, such as a serum protein, may be carried out in the presence of additional physiologically relevant components. In particular embodiments, the additional component is a lipid, such as cholesterol or triglycerides. In particular embodiments, the additional component is an HDL or LDL complex substantially free of any proteinaceous component other than the capture polypeptide.

BRIEF DESCRIPTION OF THE DRAWINGS

FIG. 3 shows a list of serum proteins which bind to PI-2301 or Copaxone. The origin of serum proteins is either normal mouse serum or normal human serum, as indicated. PI-2301 may be acetylated or non-acetylated. Binding complexes of PI-2301 or Copaxone are recognized by anti-YFAK or anti-YEAK antibodies, and detected with secondary antibodies and detection reagents. Serum proteins are eluted from the complex and identified. Proteins are assigned a score based on the A450 absorbance of the detection reagent. A score of 70 corresponds to a p=0.001, as compared to background absorbance, and is considered statistically significant.

FIG. 4 shows YEAK in the serum of mice dosed IV with 4 mg/kg of YEAK or SC with 21 mg/kg using the A450 colorimetric absorbance of HRP conjugated anti-YEAK antibodies after YEAK has bound to its target comprised of YEAK peptides bound to serum proteins contained in normal human serum. The Figure shows that GA (glatiramer acetate) fragments reach maximum serum concentration of 1800 ng/mL at around 15 min post dosing. The estimated bioavailability of Copaxone® administered SC was 12% as compared to Copaxone® administered IV. GA fraction was still detected in serum at 2 hours post-dosing.

FIG. 5 shows an example of the acute release of soluble factors in serum or plasma in response to YEAK administration in mice, in this case CCL22, also known as MDC. As seen in the figure, there exists a linear correlation between the dose of YEAK administered SC to mice, and the observed maximum CCL22 plasma concentration.

FIG. 6 shows peptide patterns observed by LC-MS from serum proteins eluted from YEAK fragments immobilized on a CNBr-Seph column. Peptide sequences were identified using the search engine Mascot. Briefly, YEAK fragments generated by tryptic enzyme digestion were coupled to Cyanogen Bromide Sepharose (CNBr-Seph) 4b, and incubated for two hours at room temperature with either human or mouse sera. Serum proteins bound to the YEAK fragments were eluted using a solution of 0.1M Glycine-HCL, pH 2.8, and digested with trypsin in 50% methanol/50 mM ammonium bicarbonate, dried, separated using liquid chromatography (LC), desolvated, ionized, sprayed into a mass spectrometer (MS), visualized, and identified using the Mascot search engine.

FIG. 7 shows an ELISA assay using methods of the instant invention depicted in FIG. 1 where YEAK was spiked into male and female normal human sera and pooled male and female normal human sera. The assay demonstrates a linear range detecting YEAK in sera of between 1 and 100 ng/ml. This assay can not be replicated using sera from mice, nor when irrelevant controls such as anti-Keyole Limpet Hemocyanin (KLH) polyserum was used.

FIG. 8 shows an SE-HPLC profile of Copaxone® (YEAK) lots P53218, and 119142 with the molecular weights demonstrated to have similar profiles.

FIG. 9 shows the two lots of Copaxone® seen in FIG. 8 used in methods of the instant invention depicted in FIG. 1.

FIG. 10 shows the two lots of Copaxone® used in FIGS. 8 and 9 in a bioassay where the monocyte cell line RAW264.7 exposed to YEAK released CCL22 in a concentration dependent manner.

FIG. 11 shows using MALDI-TOF the strict linear relationship between the actual and theoretical mean molecular weights of YEAK copolymers of different defined lengths. Theoretical values were calculated by multiplying the copolymer length in amino acids, i.e., 20, 40, 60 and 80, by the average molecular weight of one theoretical amino acid plus one molecule of water. The weight of one theoretical amino acid was calculated by using the respective mass of Y, E, A and K minus one molecule of water lost during amino acid coupling and the amino acid ratio of 1.0, 1.5, 4.5, 3.6

FIG. 12 shows the output ratios as normalized to 100 amino acids of YEAK copolymers of different lengths manufactured by solid phase synthesis determined by amino acid analysis, as well as the same analysis performed on the two lots of Copaxone® seen in FIGS. 8, 9, and 10.

Standard curves were generated, using YEAK copolymers of 20, 40, 60, and 80 amino acids. For comparison, a standard curve using Copaxone was also generated. FIG. 12 illustrates the relationship between size of the YEAK copolymers and detection by the competitive ELISA-based PK assays. The 20-mer YEAK copolymer has little inhibitory effect, but the standard curve generated with the 80-mer YEAK copolymer overlays the curve obtained with Copaxone.

FIG. 13 shows an ELISA assay where the Ig fraction of rabbit polyserum interacts strongly with Copaxone®, and demonstrates an increasing recognition as the length of the solid phase synthesized YEAK copolymers increases.

FIG. 14 shows an ELISA assay using a previous PK method (as described in PCT publication WO2009/075854 hereby incorporated by reference in its entirety) with solid phase synthesized YEAK copolymers, demonstrating a relationship between the size of the YEAK copolymers and detection by the methods of the previous assay system.

FIG. 15 shows the monocyte cell line RAW264.7 cultured with the solid phase synthesized copolymers of different sizes seen in FIGS. 12, 13, and 14 produce an increasing amount of CCL22 as the length of the copolymer increases.

FIG. 16 shows the ability of the two lots of Copaxone® used in FIGS. 8, 9, 10, and 12, and the solid phase synthesized YEAK copolymers of different lengths used in FIGS. 12, 13, 14, and 15 to induce ex vivo proliferation of splenocytes from mice immunized weekly for 3 weeks with 2.5 mg/kg of Copaxone®. A week after the last SC administration, spleens were collected, cell suspensions made, and the cells were cultured for 4 days with various concentrations of the different copolymers. Splenocyte proliferation was determined by measuring tritiated thymidine incorporation using methods well known in the art.

DETAILED DESCRIPTION OF THE INVENTION

Random Sequence Polymer (RSP) Compositions

Figure 1:
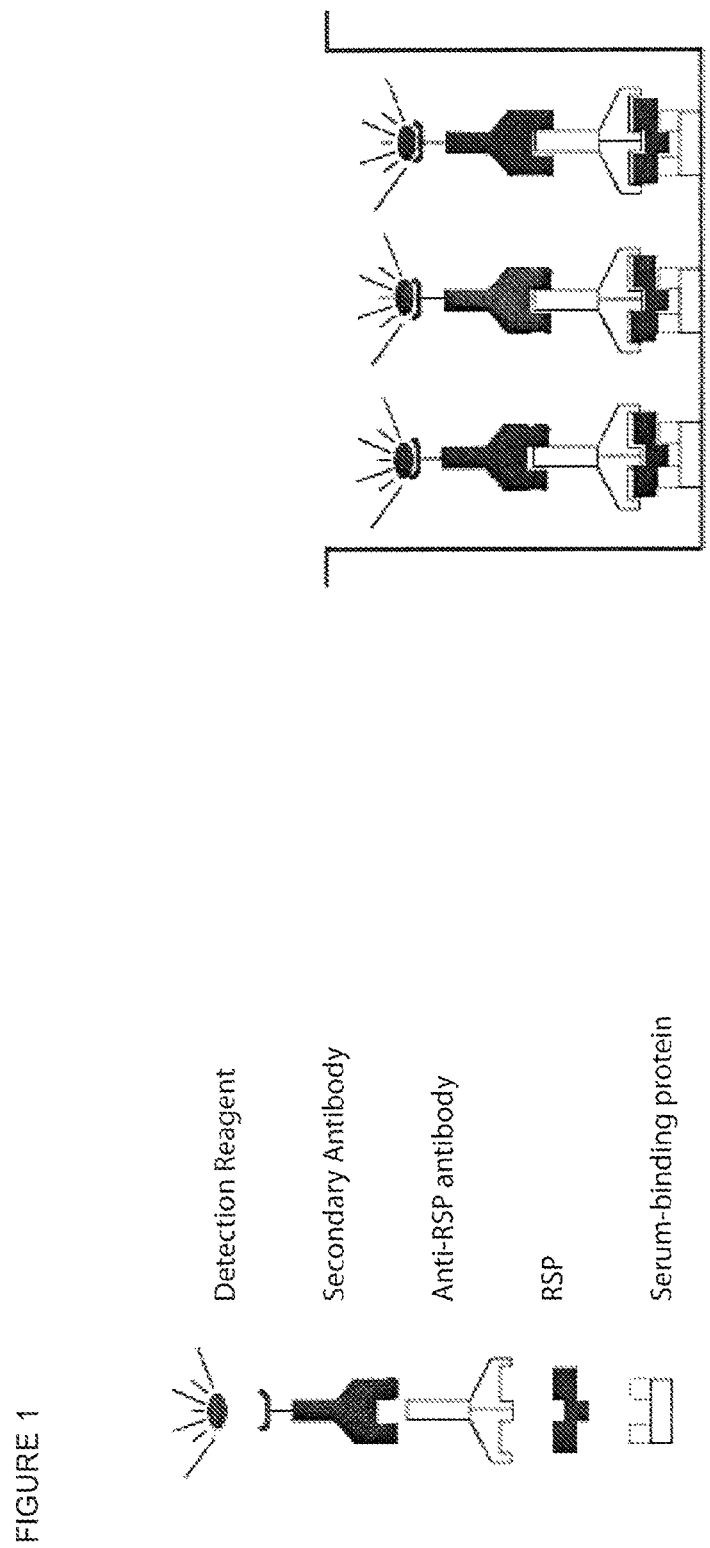
FIG. 1 is a schematic representation of an assay used to determine binding of an RSP composition to support-bound serum binding proteins. After the serum proteins have been identified, they are bound on solid-support. An RSP composition, either alone or contained within serum, is added to the support. A primary antibody against the RSP composition (or against the conjugate between the RSP composition and the serum protein) is added, and binding of the primary antibody to its target(s) is detected by a secondary antibody and detection reagent.

Random sequence polymer (RSP) compositions for the purposes of describing the instant invention may be any mixture of amino acid polymers (typically linked via peptide bonds) comprising two or more randomly ordered amino acid residues in various ratios, and are useful for invoking or attenuating certain immunological and other reactions when administered to a mammal. Because of the random diversity of the sequence mixture, a large number of peptide sequences are present in the mixture. Diversity of peptide sequences may confer increased efficacy over less diverse compositions.

An RSP composition is defined by the set of amino acids of the polymer sequence and the relative molar ratio of these amino acids. For example, YFAK designates an RSP composition consisting of tyrosine (Y), phenylalanine (F), alanine (A) and lysine (K), but does not indicate that the polymers have the amino acid sequence Y-F-A-K in that order; these amino acid residues are incorporated in a random sequence, and therefore the RSP composition comprises peptides having various sequences of Y, F, A, and K, and are free or substantially free of other amino acids. Relative molar ratio may be expressed in two ways: molar input ratio and molar output ratio. "Molar input ratio" means the molar ratio of amino acids that are used to synthesize the RSP. For example, if an RSP is said to have a molar input ratio of 1:1:10:6 of Y:F:A:K, then when synthesizing by solid phase synthesis, for each cycle of elongation, a mixture of protected amino acids Y, F, A, and K in the molar ratio of 1:1:10:6 is reacted to elongate the peptide chain. On the other hand, "Molar output ratio" means the molar ratio of amino acids as they appear in the product RSP peptides. Molar output ratio is determined by analyzing the amino acid content of an RSP composition. Input and output ratios are not identical due to differences among amino acids in incorporation efficiencies.

Suitable RSPs include those described in International PCT Publication Nos. WO 00/05250, WO 00/05249; WO 02/59143, WO 0027417, WO 96/32119, in U.S. Patent Publication Nos. US 2008/0021192, 2004/003888, 2002/005546, 2003/0004099, 2003/0064915 and 2002/0037848, in U.S. Pat. Nos. 6,514,938, 5,800,808 and 5,858,964, and those described in PCT application PCT/US05/06822. These references describe methods of synthesizing RSPs, compositions comprising RSPs, therapeutic formulations of RSPs, methods of administering RSP compositions to a subject, diseases that may be treated with RSPs, and additional therapeutically effective agents which may be co-administered to a subject in with the RSPs. Additional RSPs for use in the present invention, and methods of synthesizing them, may be found in the literature, such as in Shukaliak Quandt, J. et al. (2004) *Mol. Immunol.* 40(14-15):1075-87; Montaudo, M S (2004) *J. Am. Soc. Mass Spectrom.* 15(3):374-84; Takeda, N. et al. (2004) *J. Control Release* 95(2): 343-55; Pollino, J M et al. (2004) *J. Am. Chem. Soc.* 126(2):563-7; Fridkis-Hareli, M et al. (2002) *J. Clin Invest.* 109(12):1635-43; Williams, D M et al. (2000) *J. Biol. Chem.* 275(49): 38127-30; Tselios, T. et al. (2000) *Bioorg. Med. Chem.* 8(8): 1903-9; and Cady, C T et al. (2000) *J. Immunol.* 165(4): 1790-8. The teachings of all these patents, applications and publications are herein incorporated by reference in their entirety, particularly with respect to the structure, preparation, and function of the RSPs described therein.

Certain RSPs may comprise a suitable quantity of an amino acid of positive electrical charge, such as lysine or arginine, in combination with an amino acid with a negative electrical charge (preferably in a lesser quantity), such as glutamic acid or aspartic acid, optionally in combination with an electrically neutral amino acid such as alanine or glycine, serving as a filler, and may optionally further include an amino acid adapted to confer on the copolymer immunogenic properties, such as an aromatic amino acid like tyrosine or tryptophan. Such compositions may include any of those disclosed in WO 00/005250, the entire contents of which being incorporated herein by reference, with special attention to those portions discussing the structure, preparation, and function of the RSPs disclosed therein. In certain embodiments of the invention, an RSP composition is a mixture of polymers having randomized or partially randomized amino acid sequence and containing amino acids from the following four groups: (a) positively charged amino acids, i.e., lysine and arginine; (b) negatively charged amino acids, i.e., glutamic acid and aspartic acid; (c) small neutral amino acids, i.e., alanine, threonine, serine and glycine; and (d) bulky amino acids, i.e., leucine, isoleucine, valine, tyrosine, phenylalanine and tryptophan. Particular embodiments of such RSPs are YEAK (including Cop-1, described below), VEAK and FEAK. In other embodiments, the RSPs are terpolymers consisting of three amino acids, one selected from each of three groups among the four foregoing groups. Particular embodiments are YAK, YEK, KEA and YEA, further described below.

In other embodiments of the invention, an RSP composition is a mixture of polymers having randomized or partially randomized amino acid sequences and containing (a) glutamic acid, (b) aspartic acid, and amino acids from each of the following groups: (c) small neutral amino acids, i.e., alanine, threonine, serine and glycine; and (d) hydrophobic amino acids, i.e. valine, leucine, and isoleucine. Particular embodiments of such RSPs are DALE, DAIE, DAVE, DGLE, DGIE, and DGVE. Other embodiments of the RSPs for which the present invention is useful are those without the hydrophobic amino acids. Particular embodiments are DASE, DATE, DGSE, and DGTE.

Other suitable RSPs are mixtures of polymers having randomized or partially randomized amino acid sequences and containing amino acids from each of the following four groups: (a) negatively charged amino acids i.e., aspartic acid and glutamic acid; (b) small aliphatic amino acids, i.e., alanine and glycine; (c) hydrophobic, aliphatic amino acids i.e. leucine, isoleucine, valine, methionine; and (d) amino acids with small hydrophilic side chains (such as serine, cysteine, threonine); additionally, the copolymer may contain proline residues. In one embodiment, the copolymer is derived using the amino acids Glutamine (E) and/or Aspartic acid (D), Leucine (L), Serine (S) and Alanine (A), and is referred to herein as an "ELSA" copolymer.

In certain other embodiments, the RSPs are a mixture of randomized or partially randomized amino acid sequences containing amino acids from the following four groups: (a) negatively charged amino acids (such as aspartic acid, glutamic acid); (b) hydrophobic, aliphatic amino acids, i.e., leucine, isoleucine, valine, methionine; (c) bulky hydrophobic amino acids, i.e., tyrosine, phenylalanine; and (d) amino acids with small neutral side chains, i.e., serine, threonine alanine, glycine; additionally, the copolymer may contain proline residues. An exemplary copolymer is derived using the amino acid residues Glutamine (E) and/or Aspartic acid (D), Leucine (L), Tyrosine (Y) and Val (V), and is referred to herein as an "DLYV" copolymer.

Other particular embodiments of the RSPs are VYAK, VWAK and YFAK, which is further described below. In yet other embodiments, RSPs suitable for use with the present invention comprise amino acid residues K, E, A, S, V, and optionally, P. More preferably, the ratio of K:E:A:S:V is 0.3:0.7:9:0.5:0.5:0.3. Preferably, the RSPs are about 10 to 100 amino acid residues long, more preferably 20 to 80 amino acid residues long, even more preferably 40 to 60 amino acid residues long, and most preferably about 50 amino acid residues long. A typical preparation of RSPs is a mixture of peptides of various lengths, the majority of which are of the desired length, but may contain certain shorter or longer peptides.

A specific RSP suitable for the compositions and methods described herein is YEAK, which comprises in combination L-alanine (A), L-glutamic acid (E), L-lysine (K), and L-tyrosine (Y), and has a net overall positive electrical charge. One particular example is Copolymer 1 (Cop-1) also referred to as glatiramer acetate. Cop-1 has been approved in several countries for the treatment of multiple sclerosis (MS) under the trade name, COPAXONE™ (trademark of Teva Pharmaceuticals Ltd., Petah Tikva, Israel). Since Cop-1 is a mixture of random polypeptides, it may be that all or only a subset of the included peptides are "active." A Cop-1 RSP of interest has a molecular weight of about 2,000 to about 40,000 daltons, and more particularly from about 2,000 to about 13,000 daltons. Cop-1 has an average molecular weight about 4,700 to about 13,000 daltons, but includes smaller and larger peptides as well. The average molecular weight of most interest for Cop-1 is between about 5,000 and about 9,000 daltons. Thus, the Cop-1 RSP may be a polypeptide from about 15 to about 100 amino acid residues, preferably from about 40 to about 80, amino acid residues in length. In a particular embodiment, the length of Cop-1 RSP is between 35 and 75 amino acids residues. More particularly, the length of Cop-1 RSP is between 35 and 65 amino acid residues. In a particular embodiment the length of Cop-1 is about 50 amino acids. In another particular embodiment, the length of Cop-1 RSP is about 52 amino acids. In certain embodiments, Cop-1 has an average molar output ratio of about 1.0:2.0:6.0:5.0 for Y:E:A:K respectively, synthesized either by solution phase or solid phase chemistry well known in the art. In contrast to traditional peptide synthesis and similarly to preparation of other RSPs, the synthesis of Cop-1 is carried out by adding a mixture of appropriately protected Y, E, A, and K at a defined ratio, rather than a single amino acid, for each cycle. The variability in the output ratios comprises a range of about 10% between the different amino acids. Molecular weight ranges and processes for making a preferred form of Cop-1 are described in U.S. Pat. No. 5,800,808, the contents of which are hereby incorporated in the entirety, and particularly with respect to the structure, preparation, and function of the described RSPs.

In certain embodiments of Cop-1 RSP of about 52 amino acid residues, the ratio of alanine composition in amino acid positions 31-52 is greater than in amino acid positions 11-30, and the ratio of alanine composition in amino acid positions 11-30 is greater than in amino acid positions 1-10. In a particular embodiment, residues 1-10 of the Cop-1 RSP sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0, all ratios indicated for molar ratio among Y, E, A, K in that order.

For the purpose of the present invention, the phrase "Cop-1 or a Cop-1-related peptide or polypeptide" is intended to include any peptide or polypeptide that cross-reacts functionally with myelin basic protein (MBP) and is able to compete with MBP on the MHC class II in the antigen presentation. The activity of Cop-1 for the utilities disclosed herein is expected to remain if one or more of the following substitutions is made: aspartic acid (D) for glutamic acid (E), glycine (G) for alanine (A), arginine (R) for lysine (K), and tryptophan (W) for tyrosine (Y).

In other embodiments, the RSP composition contains three different amino acids from the groups: (a) negatively charged amino acids (such as aspartic acid, glutamic acid); (b) hydrophobic, aliphatic amino acids, i.e., leucine, isoleucine, valine, methionine; (c) bulky hydrophobic amino acids, i.e., tyrosine, phenylalanine; and (d) amino acids with small neutral side chains, i.e., serine, threonine alanine, glycine; additionally, the copolymer may contain proline residues. These copolymers are herein referred to as "terpolymers." The average molecular weight is between 2,000 to about 40,000 daltons, and preferably between about 3,000 to about 35,000 daltons. In a more particular embodiment, the average molecular weight is about 5,000 to about 25,000 daltons. Exemplary terpolymers are shown in the table below. The average molar fraction of the amino acids in these terpolymers can vary and are shown as general ranges.

TABLE A

Terpolymers suitable for the use in the present invention

| Amino acid composition | Molar fraction range (output) | Particular embodiment ratio | Reference and notes |
|---|---|---|---|
| tyrosine, alanine, and lysine, ("YAK") | Y: about 0.005 to about 0.250<br>A: about 0.3 to about 0.6<br>K: about 0.1 to about 0.5 | Y: about 0.10<br>A: about 0.54<br>K: about 0.35 | Fridkis-Hareli M., Hum Immunol. 2000; 61(7): 640-50. |
| tyrosine, glutamic acid, and lysine ("YEK") | Y: about 0.005 to about 0.250<br>E: about 0.005 to about 0.300<br>K: about 0.3 to about 0.7 | Y: about 0.26<br>E: about 0.16<br>K: about 0.58 | Variations:<br>Y -> W;<br>E -> D; and/or<br>K -> R. |
| lysine, glutamic acid, and alanine ("KEA") | K: about 0.2 to about 0.7<br>E: about 0.005 to about 0.300<br>A: about 0.005 to about 0.600 | K: about 0.36<br>E: about 0.15<br>A: about 0.48 | |
| tyrosine, glutamic acid, and alanine, ("YEA") | Y: about 0.005 to about 0.250<br>E: about 0.005 to about 0.300<br>A: about 0.005 to about 0.800 | Y: about 0.21<br>E: about 0.14<br>A: about 0.65 | Variations:<br>Y -> W;<br>E -> D; and/or<br>A -> G. |
| For reference: tyrosine, glutamic acid, alanine, lysine, ("YEAK; Cop-1") | | Y: about 0.10<br>E: about 0.14<br>A: about 0.43<br>K: about 0.34 | |

In particular embodiments, the molar fraction of amino acids of the terpolymers is similar to that preferred for Cop-1, e.g., glutamic acid about 0.14, alanine about 0.43, tyrosine about 0.10, and lysine about 0.34.

Other suitable RSPs comprise in combination L-alanine (A), L-phenylalanine (F), L-lysine (K), and L-tyrosine (Y), and herein referred to as YFAK. The length of any of such RSP is between about 25 and 300 amino acid residues. YFAK RSP that is preferred for the use in a therapeutic composition is between 35 and 75 amino acid residues. More preferably, the length of the RSP is between 35 and 65 amino acid residues. A preferred RSP has a length of about 50 or 52 amino acids.

A particular composition of YFAK (L-tyrosine, L-phenylalanine, L-alanine and L-lysine) has a molar output ratio of about 1.0:1.2:$X_A$:6.0 respectively, wherein $X_A$ is greater than 11.0 and less than 30.0, and more particularly, greater than 20.0 and less than 30.0, and the variability in the output ratios comprises a range of about 10% between the different amino acids. The molar output ratios of YFAK of random copolymers preferred for therapeutic use are shown in Table B below:

TABLE B

Amino Acid Composition Ratios of YFAK RSP

| Y | F | A | K |
|---|---|---|---|
| 1.0: | 1.2: | 11.0 < 30.0: | 6.0 |
| 1.0: | 1.2: | 18.0: | 4.0 |
| 1.0: | 1.2: | 18.0: | 5.0 |
| 1.0: | 1.2: | 18.0: | 6.0 |
| 1.0: | 1.2: | 18.0: | 7.0 |
| 1.0: | 1.2: | 18.0: | 8.0 |
| 1.0: | 1.2: | 20.0: | 4.0 |
| 1.0: | 1.2: | 20.0: | 5.0 |
| 1.0: | 1.2: | 20.0: | 6.0 |
| 1.0: | 1.2: | 20.0: | 7.0 |
| 1.0: | 1.2: | 20.0: | 8.0 |
| 1.0: | 1.2: | 20.0 < 30.0: | 6.0 |
| 1.0: | 1.2: | 22.0: | 6.0 |
| 1.0: | 1.2: | 24.0: | 6.0 |
| 1.0: | 1.2: | 26.0: | 6.0 |
| 1.0: | 1.2: | 28.0: | 6.0 |
| 1.0: | 1.2: | 30.0: | 6.0 |
| (Y + F = 2.2): | | 18.0: | 6.0 |
| 1.0: | 1.3: | 24.0: | 6.0 |
| 0.66: | 1.54: | 18.0: | 6.0 |
| 0.88: | 1.32: | 18.0: | 6.0 |

A particular YFAK composition has an average molar output ratio of about 1.0:1.3:24.0:6.0 (Y, F, A, K respectively), and may be prepared by solid phase synthesis as is known in the art.

Another YFAK composition that is preferred for therapeutic use has an average molar output ratio of YFAK about 1.0:1.2:$X_A$:6.0, wherein $X_A$ is greater than 20.0, and the ratio of alanine increases with the length of copolymer. In a particular composition, the length of such RSP is about 52 amino acid residues, and the ratio of alanine in amino acid positions 31-52 is greater than in amino acid positions 11-30, and the ratio of alanine in amino acid positions 11-30 is greater than in amino acid positions 1-10.

RSPs can be classified according to their preferential binding targets and their physiological functions, which derive directly from the amino acid composition and their ratios. Any available method can be used to ascertain whether an RSP composition binds to a candidate or known target proteins. For example, the polypeptide can be labeled with a reporter molecule (such as a radionuclide or biotin), mixed with a crude or pure preparation of a target protein and binding is detected if the reporter molecule adheres to the target protein after removal of the unbound polypeptide.

RSPs may comprise any amino acid residues in any ratios and potentially have a variety of physiological effects, but certain RSPs have recognized immunological activities. Certain RSPs are designed so that they preferentially interact with specific T cell epitopes, some of which may be directly associated with pathological disorders. One class of RSP for which the instant invention is useful is specific to T cells, which may secrete soluble mediators, such as cytokines. Preferably, such RSPs are a mixture of peptides comprising between two and eight kinds of amino acids and preferentially interact with specific T cell epitopes, some of which are or are thought to be directly associated with pathological disorders that are exacerbated by aberrant production of soluble mediators, such as cytokines.

Another class of RSP has the potential to functionally interact with thousands, preferably hundreds of thousands, more preferably millions, of T cell epitopes via presentation by MHC molecules, preferably MHC class II molecules. MHC class II alleles in human consist of HLA-DR, HLA-DQ, or HLA-DP molecules. There are also numerous alleles encoding each type of these HLA molecules. The Class II MHC molecules are expressed predominantly on the surfaces of B lymphocytes and antigen presenting cells such as macrophages. The Class II MHC protein consists of approximately equal-sized α and β subunits, both of which are transmembrane proteins. A peptide-binding cleft is formed by parts of the amino termini of both α and β subunits. This peptide-binding cleft is the site of presentation of the antigen to T cells. Certain allelic variants of the MHC class II proteins are associated with autoimmune and other aberrant immunological disorders.

One particular such disorder is multiple sclerosis (MS). MS-associated HLA-DR2 (DRB1*1501) molecules bind to myelin basic protein (MBP) with a high affinity, causing T cells to attack the myelin sheath. Cop-1, described above, binds with high affinity and in a peptide-specific manner to purified HLA-DR2 (DRB1*1501), HLA-DR1 (DRB1*0101) and HLA-DR4 (DRB1*0401). Other RSPs, such as YFAK, can also have similar or greater affinity for the antigen binding groove of such MHC class II protein than does Cop-1. Hence, these RSPs can inhibit binding of or displace the binding of myelin autoantigens from the MHC class II protein.

Similarly, an RSP composition used in the methods described herein may be useful in treating an arthritic condition, for example, rheumatoid arthritis (RA) or osteoarthritis (OA). HLA-DR1 (DRB1*0101) or HLA-DR4 (DRB1*0401), which bind to Cop-1, are associated with rheumatoid arthritis (RA). Cop-1, YFAK, and other RSPs for which this invention is useful can have a greater affinity for the antigen binding groove of such HLA than does a type II collagen 261-273 peptide, the target of rheumatoid arthritis pathology. Hence, these RSPs can inhibit binding of or displace the type II collagen 261-273 peptide from the antigen binding groove of an MHC class II protein.

Other RSPs, for which certain embodiments of the method of invention are useful, are the RSPs that bind to HLA-DQA 1 molecules, and in even more preferably to one or more of HLA molecules encoded in the alleles DQA1*0501-DQB1*0201, DQA1*0301, DQB1*0401, and DQA1*03-DQB1*0302.

In particular embodiments, the RSPs bind to certain HLA-DQ molecules that predispose the carrier of such molecules to autoimmune-associated diseases, such as type I diabetes and celiac disease, with a dissociation constant ($K_d$) at least 10 times less than the copolymer's $K_d$ for binding HLA-DR molecules and/or other DQ isotypes. Such HLA-DQ molecules are the combined protein products of specific HLA-DQB1 and DQA1 alleles known as DQB1*0201, DQB1*0302, DQB1*0304, DQB1*0401, DQB1*0501, DQB1*0502; and DQA1*0301, DQA1*0302, DQA1*0303, and DQA1*0501. These alleles may be encoded on the same haplotypes ("cis" alleles) such as DQB1*0201-DQA1*0501-DRB1*0301 and DQB1*0302-DQA1*0301-DRB1*0401. The resulting HLA molecule comprising polypeptide products of "cis" alleles is referred to as a "cis dimer." Alternatively, the alleles may be encoded on different haplotypes ("trans" alleles). HLA molecules comprising polypeptide products of "trans" alleles are referred to as "trans" dimer. An example of "trans" alleles is the combination of DQB1*0201 on DQB1*0201-DQA1*0501-DRB1*0301 and DQA1*0301 on DQB1*0301-DQA1*0301-DRB1*0404.

In particular embodiments, RSP compositions useful for the present invention bind to one or more DQ isotypes with an average $K_d$ of 1 µM or less, and more preferably an average $K_d$ less than 100 nM, 10 nM or even less than 1 nM. Another way to identify preferred copolymers is based on the measure of a copolymer to displace another in competitive binding assays, such as described in Sidney et al., 2002, J. Immunol. 169: 5098, which is expressed as an $IC_{50}$ value. Preferred RSPs of the present invention have $IC_{50}$'s less than 1 µM, more preferably less than 500 nM, and even more less than 100 nM. Some RSPs that have specificity towards HLA-DQ are ELSA and VLYV.

In certain other embodiments, methods of the invention relate to RSPs having certain characteristics of APLs based on epitopes associated with diseases.

In certain embodiments, the RSPs useful for the instant invention are formulated for use as a medicament so as to have a polydispersity less than 25,000, and more preferably less than 10000, 5000, 1000, 500, 100, 50, or even less than 10.

Pharmacokinetic Methods

In some embodiments, the absorption and distribution of RSP compositions may be determined. The rate at which an RSP composition effects a change and the persistence of the effect, as well as chemical alterations to the composition of the RSP composition may also be determined.

Certain RSP compositions persist much longer in the serum and other biological fluids than other mixtures. For example, a preparation of YFAK, PI-2301, is found at 10 times the serum concentration in comparison to Cop-1 administered at the same initial weight-by-volume concentration (US App. Pub. 2009-0275496). In some instances, the administered peptides are sequestered by or bound to some in vivo component in situ, the result of which is longer half-life in that environment, with or without enhancement in bioavailability. In certain embodiment, the environment is blood plasma or lymph. In an alternative embodiment, the environment is spinal or cerebral fluid. In yet other embodiments, the environment is any tissue or organ locale to which peptides from RSP compositions are delivered.

Identification of Physiological Polypeptides and Proteins that Bind Amino Acid Polymers from RSP Compositions One aspect of the present invention is identification of a capture polypeptide that binds an RSP composition. The term "capture polypeptide" is used herein to mean any polypeptide, protein, protein fragment, proteolipid, or other molecule containing proteinaceous material, found in normal tissues and organs. It may be a single polypeptide or a protein comprising multiple polypeptides and/or subunits, or a complex comprising a protein associated (covalently or non-covalently) with other materials such as lipids, which may further have defined structures that are desirable or necessary for the capture polypeptide to bind an RSP composition. Often a capture polypeptide is not transient, i.e., there is a base, stable amount that is found at all times, regardless of whether there is an induced or enhanced presence transiently. Preferably, a capture polypeptide is a protein. More preferably, a capture polypeptide is a protein found in a biological fluid, such as a serum protein.

Some embodiments of this aspect of the invention are methods of identifying a capture polypeptide that binds to peptides that compose an RSP composition, wherein the methods comprise: contacting a sample containing an amount of the RSP composition with a normal tissue sample; and detecting binding of the peptides of the RSP composition to any component of the normal tissue sample. In certain embodiments, the peptides of RSP composition are immobilized either on a resin (through covalent bond by reacting the peptides with activated resin) or on a solid substrate such as polystyrene. For example, a tissue sample may be contacted with the immobilized peptides and incubated, washed to remove non-specific binding, and the materials bound to the peptides that were in the tissue sample identified. The bound materials may be identified by any suitable method, such as by subjecting the materials to a panel of specific antibodies; microsequencing of materials if such materials are suspected to be polypeptides or nucleotides; tryptic digestion followed by liquid chromatography coupled with tandem mass spectrometry (LC-MS/MS) subjecting such materials to specific dyes if such materials are suspected to be polysaccharides; or any analytical method with sufficiently high sensitivity.

As a non-limiting example of the above described identification, PI-2301 or Cop-1 may be used in a direct ELISA assay (see Materials and Methods) to identify serum proteins that bind to the RSP composition comprising YFAK or YEAK peptides. Table C below lists serum proteins experimentally shown to bind to YEAK and/or YFAK peptides in normal human serum. It has been observed that YEAK and YFAK peptides have different binding specificities; conversely, serum proteins can be said to bind YEAK and YFAK peptides with different specificities. Tables D and E list serum proteins which associate with HDL and LDL, respectively. Any serum proteins may bind to the RSP composition described herein by varying affinities and selectivities.

Once a capture polypeptide that binds peptides that compose RSP compositions is identified, the specificity of the binding against similar peptides or against completely random peptides may be determined. The identified and characterized capture polypeptide (either the same molecules actually identified or like molecules obtained from a different source) then in turn may be used to quantitatively analyze the RSP compositions that it was found to bind.

Serum Proteins

In some embodiments, binding of RSP compositions to serum proteins constitutes an important aspect of their biological activity. The binding of RSP compositions to serum proteins may facilitate their tissue distribution and capture by antigen-presenting cells such as monocytes and macrophages. As stated above, binding of peptides to serum proteins may protect them from degradation and/or turnover. For example, PI-2301 (plovamer, a YFAK RSP) and Cop-1 (glatiramer acetate, a YEAK RSP) can be detected in serum of various species, including man, several hours after subcutaneous administration, whereas a control RSP disappeared from serum after a short time [US App. Pub. 2009-027496].

Accordingly, serum proteins may be used to capture and/or identify one or more peptides from an RSP composition. As a whole, RSP compositions contain many different individual peptides, of which one or more sub-fractions may be responsible for the serum protein binding properties, while other sub-fractions are not. This is especially true for mixtures made by solution phase peptide synthesis, where different lots of RSP compositions may contain variations in the percentage of peptides capable of binding serum proteins. For example, it may be important to monitor generic variants of glatiramer acetate in serum to demonstrate bioequivalence of the variants and demonstrate that the serum protein-binding fractions are equivalent quantitatively and qualitatively across different lots of RSP compositions.

Serum proteins may be used in vitro to select and/or characterize binding partners from an RSP composition. Serum proteins may also be used in vivo to select, measure, and/or otherwise characterize peptides which bind the serum proteins, thus providing a means for distinguishing specific peptides or subsets of peptides on the basis of their binding to serum proteins and/or their persistence in vivo. Specific characteristics of peptides that bind to serum proteins may comprise specific amino acid sequences, ratios of amino acids in the mixture, structures, unique motifs, configuration of charged residues. For example, the binding of PI-2301 to the lipoproteins found complexed in HDL or LDL may be possible because of the interaction of positive lysines to negatively charged residues on the outer part of the lipoproteins and the interaction of alanines and phenylalanines with the hydrophobic portion of the lipoproteins.

TABLE C

Examples of serum proteins experimentally shown to bind to YEAK and YFAK peptides in human serum:

| Protein | NCBI locus/ Accession No. |
|---|---|
| alpha-1-antitrypsin (SEQ ID NO: 1) | AAA51546 (CAJ15161) |
| alpha-1-B-glycoprotein (SEQ ID NO: 3) | OMHU1B |
| alpha2-HS glycoprotein | BAA22651 |
| Alpha-2-HS-glycoprotein | P02765 |
| apolipoprotein A-1 preproprotein (SEQ ID NO: 4) | AAA51747 |
| Apolipoprotein A-I (SEQ ID NO: 2) | Q9Z2L4 (AAS68227) |
| apolipoprotein A-II preproprotein (apolipoprotein D) | NP_001634 (AAB32200) |
| apolipoprotein A-IV | AAA51744 |
| apolipoprotein C-III | AAB59372 |
| apolipoprotein D (SEQ ID NO: 5) | AAB35919 |
| apolipoprotein E | AAB59518 |
| apolipoprotein J precursor | AAA51765 |
| ceruloplasmin | AAA51975 |
| Chain C, Immunoglobulin M | 2RCJ_C |
| Coagulation factor II (thrombin) | 3F68_H |
| complement component 3 | NP_058690 |
| complement component C3 | AAA85332 |
| complement component C4A | AAA51855 |
| complement factor B | AAA16820 |
| gelsolin isoform a precursor | NP_000168 |
| histidine-rich glycoprotein precursor | NP_000403 |
| Ig A1 Bur | 763134A |
| Ig J-chain | AAA58902 |
| Ig kappa chain V-III (KAU cold agglutinin) | A23746 |
| immunoglobulin lambda light chain | CAA40939 |
| inhibitor, Kunitz type proteinase | 0511271A |

TABLE C-continued

Examples of serum proteins experimentally shown to bind to YEAK and YFAK peptides in human serum:

| Protein | NCBI locus/Accession No. |
|---|---|
| inter-alpha-trypsin inhibitor family heavy chain-related protein (IHRP) | BAA07602 |
| Inter-alpha-trypsin inhibitor heavy chain H1 | Q61702 |
| Inter-alpha-trypsin inhibitor heavy chain H2 | Q61703 |
| lumican | AAB35361 |
| Prealbumin (SEQ ID NO: 6) | BAA00059 |
| trypsin inhibitor | CAA30160 |
| unnamed protein product (putative IgM heavy chain) | CAA34971 |
| unnamed protein product (putative vitronectin) | CAA28659 |
| vitronectin | AAA40558 |

TABLE D serum proteins associated with HDL

| Proteins | Accession No. |
|---|---|
| Apo A-I | P02647 |
| Apo A-II | P02652 |
| Apo A-IV | P06727 |
| Apo C-II | P02655 |
| Apo C-III | P02656 |
| Apo D | P05090 |
| Apo E | P02649 |
| Apo J | P10909 |
| Apo L1 | O14791 |
| Apo M | gi 13645390 |
| LPL | gi 3293305 |
| CETP | P11597 |
| C-RP | P02741 |
| Ceroplasmin | gi 13645230 |
| Complement component 3 | gi 13649325, |
| Haptoglobin | gi 1212947, P00738 |
| SAA | P35542 |
| SAP | P02743 |
| Transthyretin | P02766 |
| Transferrin | gi 4557871, P02787 |
| PON | P27169 |
| Complement component 1 inhibitor | P05155 |
| Macrophage stimulating factor 1 | gi 10337615 |
| Lymphocyte antigen | gi 553540 |
| Meningioma expressed antigen 5 | gi 11024698 |
| HLA-A protein | gi 13620230 |
| NOTCH1 | gi 11275980 |
| Sialic acid binding Ig-like lectin 5 | gi 13633818 |
| C-type lectin super family member1 | gi 5031637 |
| H factor 1 (complement) | gi 4504375 |
| Complement component 3 | gi 13649325, |
| Insulinoma-associated protein I A-6 | gi 14211925 |
| Latent transforming growth factor beta | gi 3327808 |
| LTBP-2 | gi 1272664 |
| Growth arrest-specific gene-6 | gi 4557617 |
| Receptors ryanodine receptor 2 | gi 13638463 |
| POU 5 domain protein | gi 12382246 |
| Plasma kallikrein B1 | gi 11436257 |
| TFPI | P10646/P48307 |
| Unnamed protein product | gi 10435007 |
| Unknown protein | gi 12653035 |
| Unknown protein | gi 12802992 |
| KIAA1095 | gi 5689527 |
| KIAA1730protein | gi 12698005 |
| KIAA0675 gene product | gi 13643803 |
| CIP-interacting zing finger protein | gi 12643326 |
| dj675G8.1(novel zinc finger protein) | gi 11137825 |
| dj733D15.1 | gi 3702137 |
| TAT-interactive protein, 72-kDa | gi 1427566 |
| dj758N20.1 (protein kinase) | gi 11493357 |
| Protein tyrosine phosphatase | gi 13645209 |
| Hypothetical protein dj1057B20.2 | gi 11034845 |
| Desmocollin | gi 13435361 |
| Coagulation factor VIII-associated protein | gi 13652210 |

TABLE D-continued serum proteins associated with HDL

| Proteins | Accession No. |
|---|---|
| IgG | gi 10334541, P99007 |
| HSA | gi 178345, P02728 |
| α-1β-glycoprotein | P04217 |

TABLE E serum proteins associated with LDL
Proteins apoE (five isoforms)
apoL-I (seven isoforms)
apoC-IV (three isoforms)
apoA-IV
apoA-I
apoM
apoC-III
b-actin
fibrinogen-g (two isoforms)
albumin (three isoforms)
Prenylcysteine lyase (two isoforms)

Binding Between Serum Proteins and RSP Compositions

Without wishing to be bound by theory, mechanistically, binding of peptides within RSP compositions, (e.g. PI-2301 and Cop-1) to the serum proteins such as lipoproteins found associated with HDL and LDL might facilitate their capture by monocytes through receptors such as SR-BI or ABCA1. This binding may induce activation of monocytes and their differentiation into anti-inflammatory cells. PI-2301 and Cop-1 differ in binding to serum proteins (see FIG. 3). One reason for the difference is that Cop-1 and generic variants of glatiramer acetates are made by solution phase peptide synthesis, thus significant variations in composition may be observed from lot to lot. In contrast, PI-2301 is manufactured by solid phase synthesis. PI-2301 has a very narrow molecular weight distribution as demonstrated by SEC-HPLC and MALDI-TOF with a tight Gaussian distribution by both methods. Thus, the great majority of the PI-2301 52-mer peptides in the mixture is likely to be functional. Cop-1 has a much broader molecular weight distribution, making it likely that some species of the mixture, such as small peptide species, in the mixture are ineffective. Consistent with that notion, PI-2301 is more potent than Cop-1 in terms of efficacy in preclinical models of multiple sclerosis and Crohn's disease and achieves greater serum exposure.

In assays for serum proteins that bind to PI-2301 or Cop-1, different subsets of serum proteins bind to YFAK and YEAK peptides (see FIG. 3).

A serum protein may bind to an RSP composition as a part of a cholesterol complex such as an HDL or LDL complex, and/or in conjunction with other proteins and polypeptides (any of which individually may also function as a capture polypeptide) that are found in association with the serum protein under physiological conditions. Thus, the methods of the invention contemplate having additional components found in the serum when binding RSP composition to a serum protein.

Detection of an RSP Composition in a Biological Sample: Determination of Bioavailability One aspect of the instant invention is a method for detecting the presence of an RSP composition in a biological sample, comprising: contacting the biological sample with at least one capture polypeptide; and detecting the presence or absence of binding of the capture polypeptide to the RSP composition, wherein the presence of binding indicates the presence of peptide components of the RSP composition in the biological sample. Further, such method can be extended to measure the amount or concentration of an RSP composition in a sample.

In some embodiments, the presence of an RSP composition (e.g., comprising YFAK or YEAK peptides) may be detected in a biological sample by contacting the biological sample with at least one capture polypeptide (e.g., comprising a peptide selected from alpha-1-antitrypsin, apolipoprotein A-I, alpha-1-B-glycoprotein, apolipoprotein A-IV, apolipoprotein D, and prealbumin); and detecting the presence or absence of binding of the capture polypeptide to the RSP composition. In this assay, the presence of binding indicates the presence of YFAK or YEAK peptides in the biological sample. Further, the invention provides methods for determining an amount of an RSP composition comprising YFAK or YEAK peptides in a biological sample, by contacting the biological sample with at least one capture polypeptide (e.g., comprising a peptide selected from alpha-1-antitrypsin, apolipoprotein A-I, alpha-1-B-glycoprotein, apolipoprotein A-IV, apolipoprotein D, and prealbumin); and quantifying a level of binding of the capture polypeptide to the RSP composition.

Other embodiments of the invention provide methods of determining the bioavailability of an RSP composition (e.g., comprising YFAK or YEAK peptides) in a subject, comprising administering to a subject a dose of a composition comprising the RSP composition; removing a biological sample from the subject; and contacting the biological sample with at least one capture polypeptide (e.g., comprising a peptide selected from alpha-1-antitrypsin, apolipoprotein A-I, alpha-1-B-glycoprotein, apolipoprotein A-IV, apolipoprotein D, and prealbumin). It is contemplated that the peptides of RSP compositions are extensively bound to a capture polypeptide in vivo. Nevertheless, for further characterization, antibodies specific against the complexes comprising peptides of an RSP composition and a capture peptide, but not each of those singly, may be used for detection of the bioavailable RSP composition.

Improvement of Dosage and Methods of Administration

Another aspect of the instant invention provides methods of administering RSP compositions to a mammalian subject, in an amount determined based on the bioavailable portion of the dosed amount as determined by the method described above or other methods described herein. In certain embodiments, the method further comprises including a control sample, performing a pharmacodynamic test to determine changes of physiological markers, such as hormones, enzymes, serum proteins, cytokines, immunomodulators, or an effector or regulator of any of these functional proteins, between the control sample and test samples by comparing the two results, and determining the dosage effective to induce the desired changes in a pharmacodynamic parameter. In certain embodiments, behavioral changes, subjective changes as reported by a subject such as amelioration of pain or a symptom of a disease, or other evidence of indirect effects are observed. In certain embodiments, said mammalian subject is a rodent, such as a mouse or rat. In other embodiments, said subject is human.

More generally, a method for treating or preventing an unwanted immune response in a subject may comprise providing an RSP composition (e.g., comprising YFAK or YEAK peptides); administering the RSP composition to a test subject; removing a biological sample from the test subject; contacting the biological sample with at least one capture polypeptide (e.g., comprising a peptide sequence selected from alpha-1-antitrypsin, apolipoprotein A-I, alpha-1-B-glycoprotein, apolipoprotein A-IV, apolipoprotein D, and prealbumin); separating peptides that bind to the capture polypeptide from the mixture; determining characteristics of the separated peptides; preparing a set of peptides with the characteristics of the separated peptides, and administering the prepared set of peptides to a subject.

In these methods, RSP compositions may be administered to a subject more than once. RSP compositions may be administered to the subject at intervals of, for example, 1, 2, 3, 4, 6, 12, 18, 24, 36, 48, or 72 hours.

Thus, some embodiments of the invention are methods of administering a suitable dose of an RSP composition (e.g., comprising YFAK or YEAK peptides) to a subject in need thereof, wherein the suitable dose is determined by administering to the subject a first dose of the RSP composition; removing a biological sample from the subject; contacting the biological sample with at least one capture polypeptide (e.g., comprising a peptide selected from alpha-1-antitrypsin, apolipoprotein A-I, alpha-1-B-glycoprotein, apolipoprotein A-IV, apolipoprotein D, and prealbumin); determining a level of the capture polypeptide in the biological sample; optionally repeating the previous steps using a second different dose; and comparing the levels to a predetermined suitable level of the RSP composition in the biological sample. Under these conditions, a suitable dose is the dose that results in the predetermined suitable level of the RSP composition in the biological sample. A suitable level of an RSP composition in a biological sample is a level at which a desirable functional read-out, or surrogate marker change, is obtained. A functional read-out can be the phenotype or function of the subject, the phenotype or function of cellular material derived from the subject, or the composition of fluids derived from the subject. In a particular embodiment, the detection step is repeated after certain time intervals to determine the time-course of bioavailability after administration. In certain embodiment, a half-life of the RSP composition as a group is determined from such time course. Examples for functional readouts in cases of YFAK or YEAK and immune response enhancement or sequestering are: increase or detection of TNFα, IL-6, CXCL1, CXCL2, and IL-12p70 as indicators of undesired immune stimulation, and increase or detection of Il-1ra, CXCL13, and CCL22 as indicators of desirable positive changes. Changes in these markers are easily determined by skills and materials known and readily available in the art.

Certain embodiments of the invention facilitate the comparison of effective doses across species. Comparison of effective doses in human and experimental animals such as mice or rats is made difficult not only by the body size difference and the difference in general metabolism, but also because it has been observed that bioavailability of a drug differs between animal species. It is an aspect of the present invention that the bioavailability of RSP compositions is correlated partly by the binding of the component peptides to serum proteins, which may allow for longer half-life and certain tissue distribution. Thus, some embodiments of the invention are methods of determining a suitable dosage of an RSP composition in a subject, such methods comprising determining a first suitable dosage of the RSP composition in an experimental animal model, wherein the first suitable dosage is such dosage that gives a favorable read-out and that corresponds to a level of RSP composition bound to a serum protein in vivo, and determining a second suitable dosage of the RSP composition in the subject by dosing the subject so that the level of RSP composition bound to the serum protein in vivo in the subject is similar or identical to the level achieved by administering the first suitable dosage to the experimental animal.

In particular embodiments, administration of an RSP composition (such as YEAK or YFAK RSPs, used to treat or prevent an unwanted immune response in a subject) may be enhanced using the methods of present invention. One method comprises administering to the subject a suitable dose of an RSP composition (e.g., comprising a YEAK or YFAK RSP composition), wherein such suitable dose is determined by administering to the subject a dose of the RSP composition; removing a biological sample from the experimental subject; contacting the biological sample with at least one capture polypeptide (e.g., selected from alpha-1-antitrypsin, apolipoprotein A-I, alpha-1-B-glycoprotein, apolipoprotein A-IV, apolipoprotein D, and prealbumin); determining a level of the capture polypeptide in the biological sample; optionally repeating all previous steps, and comparing the level(s) against a predetermined suitable level of the RSP composition in the biological sample. A suitable dosage is determined as described above, based on favorable readouts.

Peptides may be labeled by any suitable means, such as affixing fluorescent moieties, radioactive labels, forming chemical conjugates, biotinylation, adding epitope tags, or any other moiety that facilitates detection. Serum proteins acting as detector polypeptides as described above may be affixed to a solid support. After serum proteins have bound to one or more peptides from the RSP composition, the bound complex comprising the capture polypeptide bound to the RSP composition may be isolated.

Methods for isolating bound complexes may include immunoprecipitation, ELISA, immunodetection, or detection of the label the capture polypeptides. Detecting binding of the capture polypeptide to the RSP composition may be performed with antibodies to the capture polypeptide, antibodies to the RSP composition (such as anti-YFAK or anti-YEAK polyclonal antibodies), or antibodies that have been generated to recognize the bound complex.

RSP compositions may be administered subcutaneously, intramuscularly, intravenously, intranasally, or through any orifice or mucous membrane.

In some embodiments, a composition for detecting an RSP composition comprising YEAK or YFAK peptides in a biological sample may comprise at least one capture polypeptide comprising a peptide selected from alpha-1-antitrypsin, apolipoprotein A-I, alpha-1-B-glycoprotein, apolipoprotein A-IV, apolipoprotein D, and prealbumin.

Selection of Specific Peptides from within an RSP Composition

An aspect of the present invention is its use in identifying and/or isolating peptides or a subset of peptides from an RSP composition. Although one advantageous feature of the RSP compositions compared to a single-species or oligo-specific peptide samples is its heterogeneity, it is conceivable that a subset of the peptides that compose the mixture is more effective than another subset, or that a subset is in fact undesirable. Thus, the present invention provides methods for identifying and/or isolating peptides from a sample comprising an RSP composition based on the peptides' affinity to certain capture polypeptides. In particular instances, the subset may comprise peptides having one or more different amino acid sequences. In other instances, capture polypeptides may be used to classify the components of the RSP composition based on the binding specificity.

In some embodiments, a method of identifying a subset of peptides that bind to a capture polypeptide comprises preparing an RSP composition according to a protocol, contacting said RSP composition with a predetermined capture polypeptide (e.g., that is desirable as in vivo target or carrier), determining the binding of peptides within the RSP composition, identifying characteristics that differentiate the peptides that bind from peptides that do not, and preparing an improved RSP composition reflecting one or more of the differentiating characteristics.

In certain embodiments, a sample containing an RSP composition is contacted with a capture polypeptide, and the peptides that compose the RSP composition that bind to the capture polypeptide is isolated and identified. In some embodiments, the RSP composition is a YFAK RSP composition, and in a particular embodiment, the mixture is PI-2301. In other embodiments, the RSP composition is a YEAK RSP composition, and in a particular embodiment, the mixture is Cop1. In certain embodiments, an RSP composition is contacted with at least one serum protein which acts as a capture polypeptide. In more particular embodiments, such serum protein is selected from alpha-1-antitrypsin, apolipoprotein A-I, alpha-1-B-glycoprotein, apolipoprotein A-IV, apolipoprotein D, and prealbumin capture polypeptide.

The capture polypeptide may be immobilized on a solid support, and/or may be labeled by methods known in the art. Immobilization and labeling may be used in further steps of separating bound peptides from the capture polypeptides, and/or determining characteristics of isolated peptides. Such characteristics may include the amino acid sequence of a bound peptide, relative ratios of amino acids in bound peptides, configuration or disposition of charged residues in the sequence, the structure of the peptide, charge, or any other suitable characteristic.

The binding between RSP compositions and serum proteins may also be used for identifying bioavailable peptides in an RSP composition, for example bioavailable peptides comprising YFAK or YEAK peptides in a subject. Here, the RSP composition may be administered to the subject at a first time; and then, at a second time after administration, a tissue sample may be removed from the patient. In the tissue sample, peptides in the sample that bind to at least one capture polypeptide, e.g., comprising a peptide selected from alpha-1-antitrypsin, apolipoprotein A-I, alpha-1-B-glycoprotein, apolipoprotein A-IV, apolipoprotein D, and prealbumin, may be identified.

Improved Preparation of RSP Compositions

Another aspect of the invention is a method of improving the manufacturing process of a composition comprising an RSP composition. In some embodiments, an RSP composition is designed based on the foregoing method of identifying a subset of peptides that bind to a capture polypeptide. In some embodiments, the RSP composition is designed so that the amino acid composition and/or the amino acid sequence approximates that of the subset of peptides that bound to the capture polypeptide.

In certain embodiments, a method for producing an RSP composition (e.g., comprising YFAK or YEAK peptides) having reduced toxicity may comprises contacting the RSP composition with at least one capture polypeptide (e.g., comprising a peptide selected from alpha-1-antitrypsin, apolipoprotein A-I, alpha-1-B-glycoprotein, apolipoprotein A-IV, apolipoprotein D, and prealbumin); separating peptides that bind to the capture polypeptide from the mixture; determining characteristics of the separated peptides; and preparing a set of peptides with the characteristics of the separated peptides.

Similarly, a method for producing an RSP composition (e.g., comprising YFAK or YEAK peptides) having enhanced potency may comprise contacting the RSP composition with at least one capture polypeptide comprising a peptide (e.g., selected from alpha-1-antitrypsin, apolipoprotein A-I, alpha-1-B-glycoprotein, apolipoprotein A-IV, apolipoprotein D, and prealbumin); and separating peptides that bind to the capture polypeptide from the mixture; determining characteristics of the separated peptides; and preparing a set of peptides with the characteristics of the separated peptides.

In some embodiments, a desirable subset of an RSP composition may be obtained by using immobilized capture polypeptides in a preparatory scale. An RSP composition is prepared as previously contemplated and described, and contacted with immobilized capture polypeptides relevant to a desired improvement. Unbound peptides are removed by washing the sample, and bound portion of the RSP composition is eluted using appropriate dissociation condition, such as varied pH, salt concentration, or addition of organic solvents. The pooled bound portion is treated appropriately to concentrate and to remove therapeutically undesirable components, e.g. organic solvent, by evaporation or by further purification through appropriate chromatographic or crystallization or other purification methods. The subset of the RSP composition thus prepared is used as therapeutic agents.

Further, this aspect of the invention may be combined with the above-described improvements in dosage and administration. When better-tailored RSP compositions are prepared, it is anticipated that the dosage and mode of administration may be adjusted accordingly. Therefore, in alternative embodiments, a method comprises preparing an RSP composition according to a protocol, formulating a composition comprising the RSP composition, determining the bioavailable amount of the RSP composition in said composition by detecting the level or degree of functional read-out, comparing such read-out against a standard, and adjusting the protocol or formulation of the composition to obtain a desired bioavailability.

Tissue-Specific Targeting of Therapeutic Agents

Another potential use of the relationship between RSP compositions and serum proteins is tissue-specific targeting of therapeutic agents. In one embodiment, a method for preparing a therapeutic agent to a target tissue in a subject may comprise providing an RSP composition (e.g., comprising YFAK or YEAK peptides); and coupling a therapeutic agent to the RSP composition to form a conjugate.

Thus, some embodiments of the invention are methods for delivering a therapeutic agent to a specific tissue in a subject by isolating a peptide tag by contacting an RSP composition (e.g., comprising YFAK or YEAK peptides) with a tissue-specific peptide (e.g., comprising a peptide selected from alpha-1-antitrypsin, apolipoprotein A-I, alpha-1-B-glycoprotein, apolipoprotein A-IV, apolipoprotein D, and prealbumin); and separating peptides that bind to the tissue-specific peptide from the mixture; coupling the peptide tag to a therapeutic agent; and (c) administering the conjugate to a subject.

Other embodiments of the invention include a method of preparing a conjugate comprising a therapeutic agent coupled to a peptide tag, and the resulting conjugates themselves. The peptide tag contemplated herein may be, for example, a YEAK or YFAK peptide. Such a peptide may be isolated from the RSP composition on the basis of binding affinity to alpha-1-antitrypsin, apolipoprotein A-I, alpha-1-B-glycoprotein, apolipoprotein A-IV, apolipoprotein D, and prealbumin.

A therapeutic agent may be a small organic molecule or a biological macromolecule, and the specific tissue may be brain, lung, or liver tissue. The peptide tag may comprise a YEAK or YFAK peptide. The peptide tag may be coupled to the therapeutic agent by a covalent bond, inclusion complexes, ionic bonds, or hydrogen bonds. Examples of therapeutic agents useful for the practice of this invention are anti-tumor agents including antimetabolites, cytokine and growth factor inhibitors, kinase inhibitors, antiangiogenesis agents, anti-inflammatory agents, disease specific antibodies, vaccines, and antibiotics.

Standard immunological, biochemical, and molecular biology methods may be used herein and are known in the art. Examples of standard protocols can be found in, for example, Current Protocols series published by John Wiley and Sons, and all updates available to date, including Current Protocols in Molecular Biology, in Immunology, in Cell Biology, in Protein Chemistry, in Pharmacology, and others. All references and patents and patent applications cited herein are incorporated by reference in their entirety.

EXAMPLES

Example 1

Detection of PI-2301 and Cop-1 in Normal Human Serum

The RSP compositions PI-2301 (YFAK) or Cop-1 (YEAK) were made up at a concentration of 500 ng/mL and were diluted in 5% normal human serum in PBS to concentrations of 100 ng/mL, 50 ng/mL, 25 ng/mL, or 12.5 ng/mL, and added to normal human serum. Binding of the RSP compositions to serum proteins contained in the normal human serum was detected by addition of rabbit anti-YFAK or rabbit anti-YEAK antibodies.

An uncoated ELISA plate was blocked with PBS/0.1% Tween 20 for 2 hours at room temperature. PI-2301 or Cop-1 samples were serially diluted in PBS/5% normal human serum and added to the blocked and washed wells of the ELISA plate. The PI-2301 or Cop-1 in normal human serum was bound to the plate and unbound PI-2301 or Cop-1 was removed by washing the plate with PBS/0.05% Tween 20. Protein-A-purified anti-rabbit anti-PI-2301 or anti-rabbit anti-Cop-1, diluted to a suitable concentration based on the titer, was added for 1 hr at RT. After another wash step to remove the unbound rabbit anti-2301 or rabbit anti-Cop-1 antibodies, a secondary antibody, a goat anti-rabbit IgG-HRP (horse radish peroxidase conjugated antibody to rabbit IgG) was added to the well. After washing away any unbound secondary antibody, substrate for HRP was added to the wells and incubated for 15 minutes, which yielded a blue color that turns yellow when stop solution is added, the intensity of which color correlates with the amount of total PI-2301 or Cop-1 in the well. The optical density was measured at 450 nm with a ELISA plate reader and a titer curve was generated for each set of the serum samples spiked with PI-2301 and Cop-1, respectively. The limit of serum PI-2301 or serum Cop-1 detection is defined as the concentration which results in a A450 nm absorption which is 3 times above background. ELISA plate wells used to determine background are treated as described above except peptides from RSP compositions were omitted.

Figure 2:
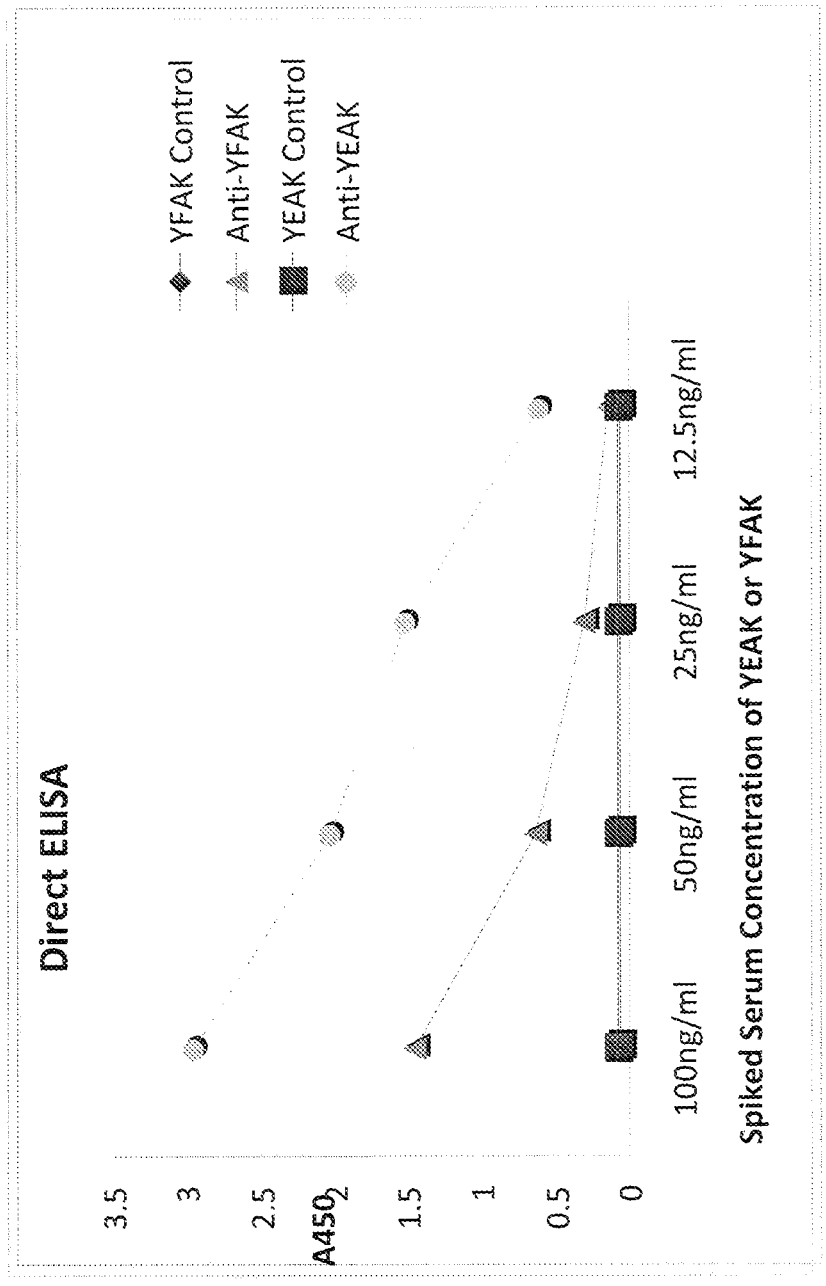
FIG. 2 shows the A450 colorimetric absorbance of HRP conjugated anti-YFAK and anti-YEAK antibodies, after the antibodies have bound to their targets. Targets comprise RSP compositions comprising YEAK or YFAK peptides bound to serum proteins contained in (or spiked into) normal human serum. At higher concentrations of RSP compositions, the detection of conjugates by anti-YEAK or anti-YFAK antibodies is higher than lower concentrations of RSP compositions. 12.5 ng/mL corresponds to a dose of approximately 2 mg in a human patient.

Results are plotted in FIG. 2. On the x-axis, the concentration of RSP composition is indicated. On the y-axis, the A450 colorimetric absorbance of HRP conjugated secondary antibodies is shown. At higher concentrations of RSP compositions, the detection of conjugates by anti-PI-2301 or anti-Cop-1 antibodies is higher than lower concentrations of RSP compositions. 12.5 ng/mL corresponds to a dose of approximately 2 mg in a human patient.

Example 2

Capture of Complexes on a Column

Immobilized RSP compositions were prepared by reacting the peptides with CNBr-activated Sepharose®, a pre-activated large pore chromatography medium used for immobilizing ligands (proteins, peptides, nucleic acids) containing primary amines using the cyanogens bromide method. Briefly, after weighing out the desired amount, the freeze-dried CNBr-Sepharose® was washed 10×15 minutes with cold 1 mM HCl (use approximately 200 mL 1 mM HCl/gram dried Sepharose) then 2× with coupling buffer. The ligand was dissolved in coupling buffer to the desired concentration, combined with the CNBr-Sepharose® in a 1:2 ratio (use 1 volume of ligand to 2 volumes of washed CNBr-Sepharose® gel) then incubated overnight at 4° C. on a rocking platform. Any remaining active sites on the gel were blocked and then washed to remove any excess ligand. To purify the ligand-specific protein, the coupled gel was washed 2× in phosphate-buffered saline (PBS), the desired reagent (serum, cell supernatant) was added in a 1:2 ratio (1 volume of reagent to 2 volumes of washed CNBr-Sepharose® gel) then incubated overnight at 4° C. on a rocking platform. The gel/reagent slurry was packed into a disposable column, washed to remove unbound reagent, then the ligand-specific protein was eluted with a low pH buffer. After pH neutralization, the absorbance at 280 nm of the eluted fractions was read to identify fractions containing the ligands. The column was washed and stored at 4° C. for repeated use.

Example 3

Identification of Proteins Bound to PI-2301 or Cop-1

Samples containing PI-2301 binding proteins or Cop-1 binding proteins were obtained by the method of Example 1 or Example 2. These samples were then enzymatically digested and analyzed by liquid chromatography tandem mass spectrometry (LC-MS/MS) for the purpose of identify the proteins which bind PI-2301 or Cop-1. Briefly, an aliquot of each sample was digested with the sequence specific protease, trypsin. After digestion, the protein peptide mixture was analyzed by LC-MS/MS. Peptides were separate based on their retention to a release phase column and then sprayed into a mass spectrometer. During the spraying process the peptide picked up a +2 or +3 charge and the mass spectrometer monitors the mass overcharge ratio. If a peptide has a significant mass overcharge ratio it is then fragmented by collision with gases and the fragment patterns are recorded. These fragment patterns can then be compared to the theoretical fragment patterns of all known proteins. This molding of experimental fragment patterns to theoretical fragment patterns resulted in the identification of several lipoproteins from the HDL and LDL complexes. These lipoproteins were found both in the PI-2301 sample and the Cop-1 sample. The Cop-1 sample also had some unique proteins including complement proteins such as C3 and C4A.

FIG. 3 summarizes the serum proteins in normal mouse serum or normal human serum which were identified by binding to PI-2301 or Cop-1. PI-2301 may be acetylated or non-acetylated. The sample proteins were obtained in a method similar to that of Example 1, wherein the peptides of RSP compositions were mixed and bound to components in serum. Binding complexes of PI-2301 or Cop-1 were recognized by anti-YFAK or anti-YEAK antibodies, and detected with secondary antibodies and detection reagents. Serum proteins were eluted from the complex and identified. Proteins are assigned a score based on the A450 absorbance of the detection reagent. A score of 70 corresponds to a significance value of $p<0.001$, as compared to background absorbance, and is considered statistically significant.

Example 4

Comparison of Peptides Composition Across Various Lengths & Lots of RSP Compositions Following synthesis of RSP compositions of different lengths, for example by solid phase synthesis or by solution phase synthesis, the individual lots or batches made by the same manufacturing process, and individual batches of mixtures manufactured by different processes are tested and compared for variation using bioassays such as the release of CCL22 by the monocyte cell line RAW264.7, by ex vivo proliferation assays, and by measuring the binding of serum proteins to peptides in the RSP composition, it is possible to determine subsets of peptides or even individual peptides that are present in any given process or lot. Processes and lots of RSP compositions will be compared to determine whether the same subsets of peptides and/or types of peptides are consistently represented across the different processes and lots.

A plurality of identifying resins are prepared by immobilizing a selection of serum proteins on solid support. For analysis of Cop-1 or PI-2301, the serum proteins may be one or more of those proteins identified in Example 1 (see FIG. 3) as binding to Cop-1 or PI-2301, respectively. Other proteins further identified as binding to Cop-1 or PI-2301 may be used as appropriate. Each solid support will contain at least one serum protein, and if more than one serum protein is bound to the solid support, then the ratio of the individual serum proteins bound to a given solid support will be consistent across each identifying resin. An aliquot from each lot of Cop-1 or PI-2301 will be applied to its own solid support, under conditions that allow a subset of Cop-1 peptides or PI-2301 to bind to the serum proteins. After washing away unbound peptides, the bound peptides will be eluted. The Cop-1 peptides isolated in this manner will be further characterized for (1) presence of distinct Cop-1 peptides, (2) ratios of peptides to one another, (3) proportion of peptides that bind to the serum binding protein, relative to the total RSP composition, (4) presence of binding motifs and peptide sequences, (5) amino acid composition and ratios of amino acids, and/or other characteristics of peptides. The characteristics of isolated Cop-1 peptides from each lot will be compared with each other.

We claim:

1. A method for determining the presence of an RSP composition consisting of YFAK peptides comprising the steps:
   a. affixing one or more proteins selected from the group consisting of:
      complement component C3, apolipoprotein A-1 preproprotein, apolipoprotein A-II preproprotein (apolipoprotein D), complement component C4A, trypsin inhibitor, inter-alpha-trypsin inhibitor family heavy chain-related protein (IHRP), alpha-1-B-glycoprotein, alpha-1-antitrypsin, apolipoprotein A-IV, ceruloplasmin, apolipoprotein E complement factor B, prealbumin, apolipoprotein C-III, alpha2-HS glycoprotein, apolipoprotein J precursor, Coagulation factor II (thrombin), histidine-rich glycoprotein precursor, Alpha-2-HS-glycoprotein, gelsolin isoform a precursor, and inhibitor Kunitz type proteinase,
      to a means for quantitatively detecting said RSP composition in a sample; and
   b. determining the level of said RSP composition in said sample.

2. A method for detecting the presence of an RSP composition consisting of YFAK peptides in a biological sample, comprising:
   a. contacting the biological sample with at least one capture polypeptide selected from the group consisting of:
      complement component C3, apolipoprotein A-1 preproprotein, apolipoprotein A-II preproprotein (apolipoprotein D), complement component C4A, trypsin inhibitor, inter-alpha-trypsin inhibitor family heavy chain-related protein (IHRP), alpha-1-B-glycoprotein, alpha-1-antitrypsin, apolipoprotein A-IV, ceruloplasmin, apolipoprotein E, complement factor B, prealbumin, apolipoprotein C-III, alpha2-HS glycoprotein, apolipoprotein J precursor, Coagulation factor II (thrombin), histidine-rich glycoprotein precursor, Alpha-2-HS-glycoprotein, gelsolin isoform a precursor, and inhibitor Kunitz type proteinase; and
   b. detecting the presence or absence of binding of the capture polypeptide to the RSP composition, wherein the presence of binding indicates the presence of YFAK peptides in the biological sample.

3. A method for measuring an amount of an RSP composition consisting of YFAK peptides in a biological sample, comprising:
   a. contacting the biological sample with at least one capture polypeptide selected from the group consisting of:
      complement component C3, apolipoprotein A-1 preproprotein, apolipoprotein A-II preproprotein (apolipoprotein D), complement component C4A, trypsin inhibitor, inter-alpha-trypsin inhibitor family heavy chain-related protein (IHRP), alpha-1-B-glycoprotein, alpha-1-antitrypsin, apolipoprotein A-IV, ceruloplasmin, apolipoprotein E, complement factor B, prealbumin, apolipoprotein C-III, alpha2-HS glycoprotein, apolipoprotein J precursor, Coagulation factor II (thrombin), histidine-rich glycoprotein precursor, Alpha-2-HS-glycoprotein, gelsolin isoform a precursor, and inhibitor Kunitz type proteinase;
   b. quantifying a level of binding of the capture polypeptide to the RSP composition;
   wherein the level of binding indicates the amount of the RSP composition in the biological sample.

4. A method for measuring bioavailability of an RSP composition consisting of YFAK peptides in a mammal, comprising:
   a. administering to a mammal a dose of a composition comprising the RSP composition;
   b. removing a biological sample from the subject; and
   c. contacting the biological sample with at least one capture polypeptide selected from the group consisting of:

complement component C3, apolipoprotein A-1 preproprotein, apolipoprotein A-II preproprotein (apolipoprotein D), complement component C4A, trypsin inhibitor, inter-alpha-trypsin inhibitor family heavy chain-related protein (IHRP), alpha-1-B-glycoprotein, alpha-1-antitrypsin, apolipoprotein A-IV, ceruloplasmin, apolipoprotein E, complement factor B, prealbumin, apolipoprotein C-III, alpha2-HS glycoprotein, apolipoprotein J precursor, Coagulation factor II (thrombin), histidine-rich glycoprotein precursor, Alpha-2-HS-glycoprotein, gelsolin isoform a precursor, and inhibitor Kunitz type proteinase;

in an immunoassay that quantitatively detects the presence of the RSP composition;

thereby determining the bioavailability of the RSP composition in the biological sample, wherein the level of the RSP composition in the biological sample is indicative of the bioavailability of the RSP composition.

5. A method for determining a suitable dose of an RSP composition consisting of YFAK peptides to administer to a subject in need thereof, comprising:

a. administering to the subject a dose of the RSP composition;

b. removing a biological sample from the subject;

c. contacting the biological sample with at least one capture polypeptide selected from the group consisting of: complement component C3, apolipoprotein A-1 preproprotein, apolipoprotein A-II preproprotein (apolipoprotein D), complement component C4A, trypsin inhibitor, inter-alpha-trypsin inhibitor family heavy chain-related protein (IHRP), alpha-1-B-glycoprotein, alpha-1-antitrypsin, apolipoprotein A-IV, ceruloplasmin, apolipoprotein E, complement factor B, prealbumin, apolipoprotein C-III, alpha2-HS glycoprotein, apolipoprotein J precursor, Coagulation factor II (thrombin), histidine-rich glycoprotein precursor, Alpha-2-HS-glycoprotein, gelsolin isoform a precursor, and inhibitor Kunitz type proteinase;

d. determining a level of the capture polypeptide in the biological sample;

e. optionally repeating steps (a) through (d) using a different dose; and f. comparing the levels to a predetermined suitable level of the RSP composition in the biological sample;

wherein the suitable dose is the dose that results in the predetermined suitable level of the RSP composition in the biological sample.

6. A method for treating or preventing an unwanted immune response in a subject, comprising:

a. administering to the subject a suitable dose of an RSP composition consisting of YFAK peptides, wherein such suitable dose is determined by:

(i) administering to the subject a dose of the RSP composition;

(ii) removing a biological sample from the experimental subject;

(iii) contacting the biological sample with at least one capture polypeptide selected from the group consisting of:

complement component C3, apolipoprotein A-1 preproprotein, apolipoprotein A-II preproprotein (apolipoprotein D), complement component C4A, trypsin inhibitor, inter-alpha-trypsin inhibitor family heavy chain-related protein (IHRP), alpha-1-B-glycoprotein, alpha-1-antitrypsin, apolipoprotein A-IV, ceruloplasmin, apolipoprotein E, complement factor B, prealbumin, apolipoprotein C-III, alpha2-HS glycoprotein, apolipoprotein J precursor, Coagulation factor II (thrombin), histidine-rich glycoprotein precursor, Alpha-2-HS-glycoprotein, gelsolin isoform a precursor, and inhibitor Kunitz type proteinase;

(iv) determining a level of the capture polypeptide in the biological sample;

(v) optionally repeating steps (i) through (iv) using a different dose; and (vi) comparing the level(s) against a predetermined suitable level of the RSP composition in the biological sample;

wherein a suitable dose is the dose that results in the predetermined suitable level of the RSP composition in said biological sample; wherein a suitable level of the RSP composition is at a level of a functional read-out of immune response enhancement or sequestering, wherein an increase or detection of TNFα, IL-6, CXCL1, CXCL2 and IL-12p70 indicates an undesired immune stimulation, and an increase or detection of Il-1ra, CXCL13 and CCL22 indicates a desirable immune stimulation.

7. The method of claim 2, wherein the capture polypeptide is labeled.

8. The method of claim 2, wherein the capture polypeptide is affixed to a solid support.

9. The method of claim 2, further comprising isolating a complex comprising the capture polypeptide bound to the RSP composition.

10. The method of claim 2, further comprising detecting binding of the capture polypeptide to the RSP composition with antibodies to the capture polypeptide.

11. The method of claim 2, wherein the composition is administered subcutaneously.

* * * * *

SEQUENCE LISTING

<160> NUMBER OF SEQ ID NOS: 6

<210> SEQ ID NO 1
<211> LENGTH: 418
<212> TYPE: PRT

-continued

<213> ORGANISM: Homo sapiens

<400> SEQUENCE: 1

```
Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Trp Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Lys Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400
```

```
Gln Asn Thr Lys Ser Pro Leu Phe Met Gly Lys Val Val Asn Pro Thr
                405                 410                 415

Gln Lys

<210> SEQ ID NO 2
<211> LENGTH: 267
<212> TYPE: PRT
<213> ORGANISM: Homo sapiens

<400> SEQUENCE: 2

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 3
<211> LENGTH: 474
<212> TYPE: PRT
<213> ORGANISM: Homo sapiens

<400> SEQUENCE: 3

Ala Ile Phe Tyr Glu Thr Gln Pro Ser Leu Trp Ala Glu Ser Glu Ser
1               5                   10                  15

Leu Leu Lys Pro Leu Ala Asn Val Thr Leu Thr Cys Gln Ala Arg Leu
            20                  25                  30
```

```
Glu Thr Pro Asp Phe Gln Leu Phe Lys Asn Gly Val Ala Gln Glu Pro
            35                  40                  45

Val His Leu Asp Ser Pro Ala Ile Lys His Gln Phe Leu Leu Thr Gly
 50                  55                  60

Asp Thr Gln Gly Arg Tyr Arg Cys Arg Ser Gly Leu Ser Thr Gly Trp
 65                  70                  75                  80

Thr Gln Leu Ser Lys Leu Leu Glu Leu Thr Gly Pro Lys Ser Leu Pro
                85                  90                  95

Ala Pro Trp Leu Ser Met Ala Pro Val Ser Trp Ile Thr Pro Gly Leu
               100                 105                 110

Lys Thr Thr Ala Val Cys Arg Gly Val Leu Arg Gly Val Thr Phe Leu
               115                 120                 125

Leu Arg Arg Glu Gly Asp His Glu Phe Leu Glu Val Pro Glu Ala Gln
130                 135                 140

Glu Asp Val Glu Ala Thr Phe Pro Val His Gln Pro Gly Asn Tyr Ser
145                 150                 155                 160

Cys Ser Tyr Arg Thr Asp Gly Glu Gly Ala Leu Ser Glu Pro Ser Ala
                165                 170                 175

Thr Val Thr Ile Glu Glu Leu Ala Ala Pro Pro Pro Pro Val Leu Met
                180                 185                 190

His His Gly Glu Ser Ser Gln Val Leu His Pro Gly Asn Lys Val Thr
                195                 200                 205

Leu Thr Cys Val Ala Pro Leu Ser Gly Val Asp Phe Gln Leu Arg Arg
210                 215                 220

Gly Glu Lys Glu Leu Leu Val Pro Arg Ser Ser Thr Ser Pro Asp Arg
225                 230                 235                 240

Ile Phe Phe His Leu Asn Ala Val Ala Leu Gly Asp Gly Gly His Tyr
                245                 250                 255

Thr Cys Arg Tyr Arg Leu His Asp Asn Gln Asn Gly Trp Ser Gly Asp
                260                 265                 270

Ser Ala Pro Val Glu Leu Ile Leu Ser Asp Glu Thr Leu Pro Ala Pro
                275                 280                 285

Glu Phe Ser Pro Glu Pro Glu Ser Gly Arg Ala Leu Arg Leu Arg Cys
                290                 295                 300

Leu Ala Pro Leu Glu Gly Ala Arg Phe Ala Leu Val Arg Glu Asp Arg
305                 310                 315                 320

Gly Gly Arg Arg Val His Arg Phe Gln Ser Pro Ala Gly Thr Glu Ala
                325                 330                 335

Leu Phe Glu Leu His Asn Ile Ser Val Ala Asp Ser Ala Asn Tyr Ser
                340                 345                 350

Cys Val Tyr Val Asp Leu Lys Pro Pro Phe Gly Gly Ser Ala Pro Ser
                355                 360                 365

Glu Arg Leu Glu Leu His Val Asp Gly Pro Pro Arg Pro Gln Leu
                370                 375                 380

Arg Ala Thr Trp Ser Gly Ala Val Leu Ala Gly Arg Asp Ala Val Leu
385                 390                 395                 400

Arg Cys Glu Gly Pro Ile Pro Asp Val Thr Phe Glu Leu Leu Arg Glu
                405                 410                 415

Gly Glu Thr Lys Ala Val Lys Thr Val Arg Thr Pro Gly Ala Ala Ala
                420                 425                 430
```

```
Asn Leu Glu Leu Ile Phe Val Gly Pro Gln His Ala Gly Asn Tyr Arg
            435                 440                 445

Cys Arg Tyr Arg Ser Trp Val Pro His Thr Phe Glu Ser Glu Leu Ser
450                 455                 460

Asp Pro Val Glu Leu Leu Val Ala Glu Ser
465                 470

<210> SEQ ID NO 4
<211> LENGTH: 396
<212> TYPE: PRT
<213> ORGANISM: Homo sapiens

<400> SEQUENCE: 4

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335
```

```
Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Gln Gln Gln
            370                 375                 380

Gln Glu Gln Val Gln Met Leu Ala Pro Leu Glu Ser
385                 390                 395

<210> SEQ ID NO 5
<211> LENGTH: 98
<212> TYPE: PRT
<213> ORGANISM: Homo sapiens

<400> SEQUENCE: 5

Gly Glu Ala Thr Pro Val Asn Leu Thr Glu Pro Ala Lys Leu Glu Val
1               5                   10                  15

Lys Phe Ser Trp Phe Met Pro Ser Ala Pro Tyr Trp Ile Leu Ala Thr
            20                  25                  30

Asp Tyr Glu Asn Tyr Ala Leu Val Tyr Ser Cys Thr Cys Ile Ile Gln
            35                  40                  45

Leu Phe His Val Asp Phe Ala Trp Ile Leu Ala Arg Asn Pro Asn Leu
    50                  55                  60

Pro Pro Glu Thr Val Asp Ser Leu Lys Asn Ile Leu Thr Ser Asn Asn
65                  70                  75                  80

Ile Asp Val Lys Lys Met Thr Val Thr Asp Gln Val Asn Cys Pro Lys
                85                  90                  95

Leu Ser

<210> SEQ ID NO 6
<211> LENGTH: 147
<212> TYPE: PRT
<213> ORGANISM: Homo sapiens

<400> SEQUENCE: 6

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
            35                  40                  45

Ala Met His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
            130                 135                 140

Pro Lys Glu
145
```